US009066899B2

(12) United States Patent
Ballou et al.

(10) Patent No.: US 9,066,899 B2
(45) Date of Patent: Jun. 30, 2015

(54) VACCINES

(75) Inventors: William Ripley Ballou, Rixensart (BE);
Joseph D Cohen, Rixensart (BE)

(73) Assignee: GLAXOSMITHKLINE BIOLOGICALS SA, Rixensart (BE)

( * ) Notice: Subject to any disclaimer, the term of this patent is extended or adjusted under 35 U.S.C. 154(b) by 419 days.

(21) Appl. No.: 12/673,272

(22) PCT Filed: Aug. 11, 2008

(86) PCT No.: PCT/EP2008/060505
§ 371 (c)(1),
(2), (4) Date: Feb. 12, 2010

(87) PCT Pub. No.: WO2009/021931
PCT Pub. Date: Feb. 19, 2009

(65) Prior Publication Data
US 2011/0212159 A1 Sep. 1, 2011

Related U.S. Application Data

(60) Provisional application No. 60/955,445, filed on Aug. 13, 2007, provisional application No. 60/957,338, filed on Aug. 22, 2007, provisional application No. 60/982,801, filed on Oct. 26, 2007.

(51) Int. Cl.
*A61K 39/015* (2006.01)
*A61K 39/116* (2006.01)
*A61K 39/00* (2006.01)

(52) U.S. Cl.
CPC ............. *A61K 39/015* (2013.01); *A61K 39/116* (2013.01); *A61K 2039/55572* (2013.01); *A61K 2039/55577* (2013.01); *A61K 2039/6075* (2013.01)

(58) Field of Classification Search
None
See application file for complete search history.

(56) References Cited

U.S. PATENT DOCUMENTS

| 4,235,877 | A | 11/1980 | Fullerton |
| 4,372,945 | A | 2/1983 | Likhite |
| 4,474,757 | A | 10/1984 | Arnon et al. |
| 4,837,016 | A | 6/1989 | Holder et al. |
| 4,912,094 | A | 3/1990 | Myers et al. |
| 5,057,540 | A | 10/1991 | Kensil et al. |
| 6,083,716 | A | 7/2000 | Wilson et al. |
| 2009/0053265 | A1 | 2/2009 | Corradin et al. |

FOREIGN PATENT DOCUMENTS

| BE | WO 2006/029887 | 3/2006 |
| BE | WO 2007/003384 | 1/2007 |
| EP | 0468520 | 7/1991 |
| EP | 0549074 | 12/1992 |
| EP | 0689454 | 3/1994 |
| EP | 0362279 | 1/1995 |
| EP | 0761231 | 3/1997 |
| EP | 1623720 | 2/2006 |
| GB | 2122204 | 5/1983 |
| GB | 2220211 | 5/1983 |
| WO | WO 90/01496 | 2/1990 |
| WO | WO 91/11516 | 8/1991 |
| WO | WO 91/18922 | 12/1991 |
| WO | WO 92/11868 | 7/1992 |
| WO | WO 93/10152 A1 | 5/1993 |
| WO | WO 94 00153 | 1/1994 |
| WO | WO 94/21292 | 9/1994 |
| WO | WO 95/17209 | 6/1995 |
| WO | WO 95/17210 | 6/1995 |
| WO | WO 96/02555 | 2/1996 |
| WO | WO 96/11711 | 4/1996 |
| WO | WO 96/33739 | 10/1996 |
| WO | WO 98/05355 | 2/1998 |
| WO | WO 98/15287 | 4/1998 |
| WO | WO 98/16247 | 4/1998 |
| WO | WO 98/43690 | 10/1998 |
| WO | WO 98/56414 | 12/1998 |
| WO | WO 99/10008 | 3/1999 |
| WO | WO 99/11241 | 3/1999 |
| WO | WO 99/12565 | 3/1999 |
| WO | WO 02/077195 | 10/2002 |
| WO | WO 03/046142 | 6/2003 |
| WO | WO 2004/037189 | 5/2004 |
| WO | WO 2004/044167 | 5/2004 |
| WO | WO 2006/029887 | 3/2006 |
| WO | WO 2006/040334 | 4/2006 |
| WO | WO2009/021931 A3 | 11/2008 |

OTHER PUBLICATIONS

Alonso, et al., "Efficacy of the RTS, S/AS02A vaccine against *Plasmodium falciparum* infection and disease in young African children: randomised controlled trial", *The Lancet*, 364(9444):1411-1420 (2004).

Alonso, et al., "Duration of protection with RTS,S/AS02A malaria vaccine in prevention of *Plasmodium falciparum* disease in Mozambican children: single-blind extended follow-up of a randomised controlled trial", *The Lancet*, 366(9502)2012-2018 (2005).

Alonso, et al., "Randomised trial of efficacy of SPf66 vaccine against *Plasmodium falciparum* malaria in children in southern Tanzania", *The Lancet*, 344(8931)1175-1181 (1994).

Acosta, et al., "Evaluation of the SPf66 vaccine for malaria control when delivered through the EPI scheme in Tanzania", *Tropical Medicine and International Health*, 4(5):368-376 (1999).

(Continued)

*Primary Examiner* — Jennifer Graser
(74) *Attorney, Agent, or Firm* — James T. Olesen; Jeffrey Sutton

(57) ABSTRACT

The invention relates to use of an antigen derived from the circumsporozoite protein (CS) protein of *Plasmodium falciparum* which is expressed at the pre-erythrocytic stage of malarial infection in combination with a pharmaceutically acceptable adjuvant, in the manufacture of a medicament for vaccinating infants against malaria.

15 Claims, 8 Drawing Sheets

(56) References Cited

OTHER PUBLICATIONS

Ballou, et al., "Safety and efficacy of a recombinant DNA *Plasmodium falciparum* sporozoite vaccine", The Lancet, 8545:1278-1281 (1987).

Bojang, et al., "Follow-up of Gambian children recruited to a pilot safety and immunogenicity study of the malaria vaccine SPf66", *Parasite Immunology*, 19:579-581 (1997).

Graves, et al., "Vaccines for preventing malaria (SPf66) (Review)"Cochrane Database of Systematic Reviews [Online] No. 2, Apr. 19, 2006, XP002501762 Retrieved from the Internet: URL:http://mrw.interscience.wiley.com/cochrane/clsysrev/articles/CD005966/pdf_fs.html> [retrieved on Oct. 29, 2008] p. 2, right-hand column, p. 4, right hand column, pp. 10-12.

Sacarlal, et aL, "Safety of the RTS.S/AS02A malaria vaccine in Mozambican children during a Phase IIb trial", *Vaccine*, 26(2)174-184 (2007).

Caspers, et al., "The circumsporozoite protein gene from NF54, a *Plasmodium falciparum* isolate used in malaria vaccine trials", Molecular and Biochemical Parasitology, 1989 Elsevier Science Publishers B.V., 35:185-190.

Agnandji, "Final Results of Phase 3 Trial of RTS, S/AS01 Malaria Vaccine in African Children", The New England Journal of Medicine, Massachusetts Medical Society, 365(20):1863-1875 (2011).

Agnandji, "A Phase 3 Trial of RTS,S/AS01 Malaria Vaccine in African Infants", N Engl J Med 2012, DOI:10.1056/NEJMoa1208934.

Aidoo, et al, 232 "Cytotoxic T-lymphocyte epitopes for HLA-B53 and other HLA types in the malaria vaccine candidate live-stage antigen 3", Infection and Immunity, 2000 American Society for Microbiology, 68(1):227-232.

Alonso, et al., Population and health in developing countries, vol. 1, Population, health and survival at INDEPTH sites. Ottawa: International development research center (IDRC), 2001, Chapter 15, p. 189-195.

Ballou, et al. "Update on the clinical development of candidate malaria vaccines" Am J Trop Med Hyg., 71(2_suppl):239-247, 2004 The American Society of Tropical Medicine and Hygiene.

Bojang, et al., "Safety and immunogenicity of RTS,S/AS02A candidate malaria vaccine in Gambian children", Vaccine, 2005 Elsevier Ltd., 23:4148-4157.

Bojang, et al., "Efficacy of RTS,S/AS02 malaria vaccine against *Plasmodium falciparum* infection in semi-immune adult men in The Gambia: a randomised trial", The Lancet, 2001 The Lancet Publishing Group.,358(9297):1927-1934.

Brazolot-Millan, et al., "CpG DNA can induce strong Th1 humoral and cell-mediated immune responses against hepatitis B surface antigen in young mice", PNAS, 1998 The National Academy of Sciences, 95(26):15553-15558.

Breman, et al., "The intolerable burden of malaria: what's new, what's needed", Am J Trop Med Hyg., 2004 71(2_suppl):0-i-.

Charoenvit, et al, "CD4+ T cell and gamma interferon-dependant protection against murine malaria by immunization with linear synthetic peptides from a *Plasmodium yoelii* 17 Kilodalton hepatocyte erythrocyte protein", Infection and Immunity, 1999 American Society for Microbiology, 67(11):5604-5614.

Dame, et al., "Structure of the gene encoding the immunodominant surface antigen on the sporozoite of the human malaria parasite *Plasmodium falciparum*", Science, 1984 ;225:593-9 (abstract).

Daubersies, et al., "Protection against *Plasmodium falciparum* malaria in chimpanzees by immunization with the conserved pre-erythrocytic liver stage antigen 3", Nature Medicine vol. 6 No. 11 Nov. 2000 p. 1258-1263.

Davis, et al., "CpG DNA is a potent enhancer of specific immunity in mice I munized with recombinant hepatitis B surface antigen", J. Immunol., 1998 The American Association of Immunologists, 160(2):870-876.

Doherty, et al., "A phase I safety and immunogenicity trial with the candidate malaria vaccine RTS,S/SBAS2 in semi-immune adults in The Gambia", Am J Trop Med Hyg , 1999 The American Society of Tropical Medicine and Hygiene;61(6):865-868.

Garcon et al., "Development of RTS,S/AS02 a purified subunit-based malaria vaccine candidate formulation with a novel adjuvant", Expert Rev. Vaccines, 2003 Future Drugs Ltd., 2(2):231-232.

Gordon, et al., "Safety, Immunogenicity, and Efficacy of a recombinantly produced *Plasmodium falciparum* circumsporozoite protein-Hepatitis B surface antigen subunit vaccine", J. Infectious Disease, 171:1576-1585, 1995 (abstract).

Hay, et al., "The global distribution and population at risk of malaria: past, present, and future" The Lancet Infectious Diseases, 2004 http://infectionthelancet.com; 4(6):327-336.

Heppner, et al, "Towards an RTX,S-based, multistage, multi-antigen vaccine against *Falciparum* malaria: progress at the Walter Reed Army Institute of Research", Vaccine, 2005 Elsevier Ltd, 23:2243-2250.

Herrington, et al, "Safety and immunogenicity in man of a synthetic peptide malaria vaccine against *Plasmodium falciparum* sporozoites" Nature, 1987 Nature Publishing Group, 328:257, 1987.

Kensil, "Separation and characterization of saponins with adjuvant activity from *Quillaja saponaria* Molina cortex", J. Immunology, 1991 The American Association of Immunologists, 146:431-437.

Klausner, et al., "An attack on all fronts", Nature, 2004 Nature Publishing Group;430:930-931.

Krieg, et al., "CpG motifs in bacterial DNA trigger direct B-cell activation", Nature, 1995 Nature Publishing Group, 374:546-549.

Kurtis et al., "Pre-erythrocytic immunity to *Plasmodium falciparum* the case for an LSA-1 vaccine",Trends in Parasitology vol. 17 No. 5 May 2001 p. 219-223.

Lacaille-Dubois, et al., "A review of the biological and pharmacological activities of saponins", Phytomedicine, 1996 Gustav Fischer Verlag, 12:363-386.

Loscertales, et al., "Epidemiology and clinical presentation of respiratory syncytial virus infection in a rural area of southern Mozambique", Pediatr Infect Dis J., 2002 Lippincott Williams & Wilkins, Inc., 21:148-155.

Macete, et al., "Evaluation of two formulations of adjuvanted RTS, S malaria vaccine in children aged 3 to 5 years living in a malaria-endimic regioun of Mozambique: a Phase I/Ib randomized double-blind bridging trial", Trials Mar. 26, 2007; 8:11.

McCluskie, et al., "Cutting edge: CpG is a potent enhancer of systemic and mucosal immune responses against hepatitis B surface antigen with intranasal administration to mice", J. Immunol., 1998 The American Association of Immunologists, 161(9):4463-4466.

Meraldi et al., "Natural antibody response to *Plasmodium falciparum* Exp-1, MSP-3 and GLURP long synthetic peptides and associated with protection", Parasite Immunology, 2004 Blackwell Publishing, 26, 265-272.

Mossmann, et al., TH1 and TH2 cells: different patterns of lymphokine secretion lead to different functional properties, Annual Review of Immunology, 7:145-173, 1989 Annual Reviews Inc.

Musti, et al., "Transcriptional mapping of two yeast genes coding for glyceraldehydes 3-phosphate dehydrogenase isolated by sequence homology with the chicken gene", Gene, 1983Elsevier, 25:133-143.

Polley, et al., "Human antibodies to recombinant protein constructs of *Plasmodium falciparum* apical membrane antigen 1 (AMA1) and their associations with protection from malaria", Vaccine 23, 2004 Elsevier Ltd., 718-728.

Richards, "Liposomes containing Lipid A serve as an adjuvant for induction of antibody and cytotoxic T-Cell responses against RTS,S malaria antigen", Infection and Immunity, 1998 The American Society for Microbiology, 66(6):2859-2865.

Saute, et al., "Malaria in southern Mozambique: Malariornetric indicators and malaria case definition in Manhica district", Trans R Soc Trop Med Hyg Nov.-Dec. 2003; 97(6):661-666.

Stoute, et al., A preliminary evaluation of a recombinant circumsporozoite protein vaccine against *Plasmodium falciparum* malaria. RTS,S Malaria Vaccine Evaluation Group. N Engl J Med 1997 The New England Journal of Medicine, 336(2):86-91.

Stoute, et al., "Long Term Efficacy and Immune Responses Following Immunization with the RTS,S Malaria Vaccine" J Infect Dis., 1998, 178:1139-44.

(56) References Cited

OTHER PUBLICATIONS

Stowers et al., "Vaccination of monkeys with recombinant *Plasmodium falciparum* apical membrane antigen 1 confers protection against blood-stage malaria", Infection and Immunity, Dec. 2002 p. 6961-6967.
Sun, et al., "Protective immunity induced with malaria vaccine, RTS,S, is linked to *Plasmodium falciparum* circumsporozoite protein-specific CD4(+) and CD8(+) T cells producing IFN-gamma" J Immunol. 2003 The American Association of Immunologists, Inc., 171(12): 6961-6967.
Walsh, et al., "Heterologous prime-boost immunization in rhesus macaques by two, optimally spaced particle-mediated epidermal deliveries of *Plasmodum falciparum* circumsporozoite protein-encoding DNA, followed by intramuscular RTS,S/AS02A", Vaccine, 2006 Elsevier, 24:4167-4178.
World Health Organization. Management of severe malaria, a practical handbook. Second edition, 2000. http://mosquito.who.int/docs/hbsm.pdf.
Young, et al., "Expression of *Plasmodium falciparum* circumsporozoite proteins in *Escherichia coli* for potential use in a human malaria vaccine" Science 1985; 228:958-62 (abstract).
Chulay et al, (1986) *Malaria transmitted to humans by mosquitoes infected from cultured Plasmodium falicparum*. Am J Trop Med Hyg. Jan:35(1):66-8.
Hilgers et al. (1986). *Synergistic effects of synthetic adjuvants on the humoral immune response*. Int.Arch.Allergy.Immunol., 79(4):392-6.
Hilgers et al. (1987). *Synthetic, sulpholipopolysaccharides: novel adjuvants for humoral immune responses*. Immunology, 60(1):141-6.
Hoffamn SL (1996) "Malaria Vaccine Development; a multi-immune response approach" Am Soc Microbiol Press Ed Hoffman SL, Chapter 3 "Attacking the infected hepatocyte".
Kensil, C. R. (1996) *Saponins as vaccine adjuvants*. Crit Rev Ther Drug Carrier Syst 12 (1-2):1-55.
Powell and Newman (Editors) (1995) *Vaccine Design—the subunit and adjuvant approach*. Pharmaceutical Biotechnology, vol. 61, Plenum Press New York.
Ribi et al, (1986) *Modulation of humoral and cell-mediated immune responses by a structurally established nontoxic lipid A*. Immunobiology and Immunopharmacology of bacterial endotoxins. Plenum Publ. Corp., NY, p. 407-420.
Valenzuela P, Gray P, Quiroga M, Zaldivar J, Goodman H, Rutter W. (1979) *Nucleotide sequence of the gene coding for the major protein of hepatitis B virus surface antigen*. Nature 280, 815-819.
Valenzuela, et al., "Nucleotide sequence of the gene coding for the major protein of hepatitis B virus surface antigen", Nature, 1979 Nature Publishing Group, 280:815-819, (abstract).
The work or data disclosed at the 50th Annual Meeting of the American Society of Tropical Medicine and Hygiene, Atlanta, GA Nov. 13, 2001.
The work or data disclosed at the Fourth Meeting on Novel Adjuvants in/close to Human Clinical Testing, sponsored by the WHO, Annecy, France, Jun. 23-25, 2003.
The work or data disclosed in the Abstracts of the 4th Multilateral Initiative in Malaria Meeting, Yaounde, Cameroon, Nov. 13-18, 2005.
The following publications or posters, slides and/or handouts therefrom: Kester KE. Malaria-027 trial results. WRAIR sponsored satellite presentation at ASTMH Philadelphia USA II—Dec. 15, 2005.
Holland, C. A.; Williams, J.; Momin, P.; Delchambre, M.; Dubois, M. C.; Watson, E.; Mowery, K.; Tornieporth, N.; Vigneron, L.; Voss, G.; Cohen, J.; Ballou, W. R.; Kester, K.E., Department of Immunology, Walter Reed Army Institute of Research, Washington, DC, USA, American Journal of Tropical Medicine and Hygiene, (Sep. 1999) vol. 61, No. 3, Suppl., pp. 491. print. Meeting Info. Abstract.
Ripley Ballou, W.; Cohen, Joe D. "Recent Progress with the RTS,S Malaria Vaccine", Malaria: Functional Genornics to Biology to Medicine (C5, Feb. 28, 2006, Taos, NM.) Abstract.
Aids Vaccine 2006, Aug. 29, 2006, Amsterdam, Netherland.

56th Annual Meeting of the American Society of Tropical Medicine and Hygiene (ASTMH), Nov. 4, 2007, Phila, PA.
2008 Malaria: Immunology, Pathogenesis and Vaccine Perspectives (E3) Jun. 8, 2008, Alpbach, Austria.
58th Annual Meeting of the American Society of Tropical Medicine and Hygiene (ASTMH) Nov. 18, 2009 Washington, DC; USA.
14th International Congress of Immunology (ICI) Aug. 22, 2010 Kobe; Japan.
D.M. Gordon, T.W. McGovern, U. Krzych, J.D. Cohen, Schneider, R. LaChance, D.G. Heppner, G. Yuan, M. Hollngdale, M, Slaoui, P. Hauser, P, Voet. J.C. Sadoff and W.R. Ballou: "Safety, immunogenicity and efficacy of a recombinantly produced *Plasmodium falciparum* circumsporozoite. protein-hepatitis B surface antigen subunit vaccine". J. Infect. Dis. (1995) 171:1576-1585.
J.A. Stoute, M. Slaoui, D.G. Heppner, P. Momin, K.E. Kester, P. Desmons, B.T. Wellde, N. Garçon, U. Krzych, M. Marchand, W.R. Ballou and J.D. Cohen : "A preliminary evaluation of a recombinant circumsporozoite protein vaccine against *Plasmodium falciparum* malaria". The New England Journal of Medicine (1997) 336:86-91.
J.A. Stoute, K.E. Kester, U. Krzych, B.T. Wellde, T. Hall, K. White, G. Glenn, C,F. Ockenhouse, N. Garcon, R. Schwenk, D.E. Lanar, P. Sun, P. Momin, R.A. Wirtz, C. Golenda, M. Slaoui, G. Wortmann, C. Holland, M. Dowler, J. Cohen and W.R. Ballou : "Long-term efficacy and immune responses following immunization with the RTS,S Malaria vaccine". J. Infect. Dis. (1998) 178(4)1139-1144.
A. Lalvani, P. Moris, G. Voss, A.A. Pathan, K.E. Kester, R. Brookes, E. Lee, M, Koutsoukos, M. Plebanski, M. Delchambre, K.L. Flanagan, C. Carton, M. Slaoui, C. Van Hoecke, W.R. Ballou, A.V.S. Hill and J. Cohen : "Potent induction of focused Th1-type cellular and humoral immune responses by RTS,S/SBAS2, a recombinant *Plasmodium falciparum* Malaria vaccine". J. Infect. Dis. (1999) 180:1656-1664.
J.F. Doherty, M. Pinder, N. Tornieporth, C. Carton, L. Vigneron, P. Milligan, W.R. Ballou, C.A. Holland, K.E. Kester, G. Voss, P. Mown, B.M. Greenwood, K.P.W.J. McAdam and J. Cohen : "A phase I safety and immunogenicity trial with the candidate Malaria vaccine RTS,S/SBAS2 in semi-immune adults in The Gambia". Am. J. Trop. Med. Hyg. (1999) 61(6):865-868.
A. Alloueche, H. Silveira, D.J. Conway, K. Bojang, T. Doherty, J. Cohen, M. Pinder and B.M. Greenwood : "High-throughput sequence typing of T-cell epitope polymorphisms in *Plasmodium falciparum* circumsporozoite protein". Molecular and Biochemical Parasitology (2000) 106:273-282.
K.E. Kester, D.A. McKinney, C.F. Ockenhouse, D.G. Heppner, B.T. Wellde, J.A. Stoute, B,T. Hall, U. Krzych, G.E. Poley, A. Montemarano, P.F. Sun, R. Schwenk, K. White, T. Le, C. Golenda, R.A. Gasser, D. Gordon, G. Wortmann, R.S. Miller, G.M. Glenn, J. Palensky, J. Cohen and W.R. Ballou : "Efficacy of recombinant circumsporozoite protein vaccine regimens against experimental *Plasmodium falciparum* malaria. RTS,S Malaria vaccine evaluation group". The Journal of Infectious Diseases (2001) 183:640-647.
K.A. Bojang, P.J.M. Milligan, M. Pinder, L Vigneron, A. Alloueche, K.E. Kester, W.R. Ballou, D.J. Conway, W.H.H. Reece, P. Gothard, L. Yamuah, M. Delchambre, G. Voss, B.M. Greenwood, A. Hill, K.P. W.J. McAdam, N. Tornieporth, J.D. Cohen, T. Doherty: "Efficacy of RTS,S/AS02 malaria vaccine against *Plasmodium falciparum* infection in semi-immune adult men in The Gambia: a randomised trial". The Lancet (2001) 358: 1927-34.
A. Alloueche, P. Milligan, D.J. Conway, M. Pinder, K. Bojang, T. Doherty, N. Tornieporth, J. Cohen, B.M. Greenwood: "Protective efficacy of the RTS,S/AS02 *Plasmodium falciparum* malaria vaccine is not strain specific". American Journal of Tropical & Medicine Hygiene (2003) 68 (1): 97-101.
N. Garcon, D.G. Heppener, J. Cohen: "Development of RTS,S/AS02: a purified subunit-based malaria vaccine candidate formulated with a novel adjuvant". Expert Rev. Vaccines (2003) 2 (2): 231-38.
D,G. Heppner, J.D. Cohen, J.F. Cummings, W.R. Ballou, C.F. Ockenhouse, K.E. Kester: "Adjuvanted RTS,S and other protein-based pre-erythrocytic stage malaria vaccines". In: New Generation Vaccines/3rd edition—revised and expanded—edited by M. Levine, J. Kaper, R. Rappuoli, M. Liu and M. Good (2004).
P. Sun, R. Schwenk; K. White, J. Stoute, J. Cohen, W.R. Ballou, G. Voss, K.E. Kester, D.G. Heppner, U. Krzych: "Protective immunity

(56) References Cited

OTHER PUBLICATIONS induced with malaria vaccine, RTS,S, is linked to *Plasmodium falciparum* circumsporozoite protein-specific CD4+ and CD8+ T cells producing IFN-γ". Journal of Immunol. Dec. 15, 2003:171 (2): 6961-7.

W.R. Ballou, F. Dubovsky, K.E. Kester, J. Lyon, D.E. Lanar, A. Saul, B.K. Giersing, P. Druihle, D. Carucci, T.L. Richie, G. Corradin, B.F. Hall, A.V.S. Hill, C. Diggs, M. Arevalo-Herrera, J. Cohen: "Update on the clinical development of candidate malaria vaccines", Am. J. Trop. Med Hyg. (2004) 71 (suppl 2): 239-247.

M. Pinder, W.H.H. Reece, M, Plebanski, P. Akinwunmi, K.L. Flanagan, E.A.M. Lee, T. Doherty, P, Milligan, A. Jaye, N. Tornieporth, R. Ballou, K.P.M.J. McAdam, J. Cohen, A.V.S. Hill/ "Cellular immunity induced by the recombinant *Plasmodium falciparum* malaria vaccine, RTS,S/AS02, in semi-immune adults in The Gambia". Clin Exp Immunol 2004; 135:286-293.

Epstein JE, Charoenvit Y, Kester KE, Wang R, Newcomer R, Fitzpatrick S, Richie TL, Tornieporth N, Heppner DG, Ockenhouse C, Majam V, Holland C, Abot E, Ganeshan H, Berzins M, Jones T, Freydberg CN, Ng J, Norman J, Carucci DJ, Cohen J, Hoffman SL, "Safety, tolerability, and antibody responses in humans after sequential immunization with a PfCSP DNA vaccine followed by the recombinant protein vaccine RTS,S/AS02A." Vaccine. Apr. 16, 2004;22 (13-14):1592-603.

Reece WH, Pinder M, Gothard PK, Milligan P, Bojang K, Doherty T, Plebanski M, Akinwunmi P, Everaere S, Watkins KR, Voss G, Tornieporth N, Alloueche A, Greenwood BM, Kester KE, McAdam KP, Cohen J, Hill AV. "A CD4(+) T-cell immune response to a conserved epitope in the circumsporozoite protein correlates with protection from natural *Plasmodium falciparum* infection and disease." Nat Med. Apr. 2004;10 (4):406-10, Epub Mar. 14, 2004.

Wang R, Epstein J, Charoenvit Y, Baraceros F.M., Rahardjo N, Gay T, Banania JG, Chattopadhyay R, De La Vega P; Richie TL, Tornieporth N, Doolan DL, Kester KE, Heppern DG, Norman J, Carucci D, Cohen J, Hoffman S.L. "Induction in Humans of CD8+ and CD4+ T cell and antibody responses by sequential immunization with Malaria DNA and recombinant protein" Journal of Immunol 2004; 172: 5561-5569.

P.L. Alonso, J. Sacarlal, J.J. Aponte, A. Leach, E. Macete, J. Milman, I Mandomando, B. Spiesens, S. Guinovart, M. Espasa, Q. Bassat, P. Aide, O. Ofori-Anyianam, M.M. Navia, S. Corachan, M. Ceuppens, M-C Dubois, M-A, Demoitie, F. Dubovsky, C. Menendez, N. Tornieporth, W.R. Ballou, R. Thompson, J. Cohen: "Efficacy of the RTS,S/AS02A vaccine against *Plasmodium falciparum* infection and disease in young African children: randomized controlled trial". The Lancet (2004) 364, 1411-20.

Douglas S. Walsh, Sathit Pichyangkul, Montip Gettayacamin, Pongsri Tongtawe, Claire-Anne Siegrist, Pranee Hansukjariya, Kent E. Kester, Carolyn A. Holland, Gerald Voss, Joe Cohen, Ann V. Stewart; R. Scott Miller, W. Ripley Ballou, D. Gray Heppner: Safety and immunogenicity of RTS,S+Trap malaria vaccine, formulated in the ASO2A adjuvant system, in infant rhesus monkeys. Am. J. Trop. Med. Hyg. (2004) 70 (5), 499-509.

G. Heppner, K. Kester , C. Ockenhouse, N. Tornieporth, O. Ofori , J. Lyon, A. Stewart, P. Dubois, D. Lanar, U. Krzych, P. Moris, E. Angov, J. F. Cummings, A. Leach, T. Hall, S. Dutta, R. Schwenk, C. Hillier. A. Barbosa, L. Ware, L. Nair, C. Darko, M.. Withers, B. Ogutu, M. Polhemus, M. Fukuda. S. Pichyangkul, M. Gettyacamin, C. Diggs, L. Soisson, J. Milman, M-C. Dubois, N. Garcon, K. Tucker, J. Wittes, C. Plowe, M. Thera, O. Duombo, M. Pau, J, Goudsmit, R. Ballou, J. Cohen: "Towards an RTS,S-based multi-stage, multi-antigen vaccine against *falciparum* malaria: progress at the Walter Reed Army Institute of Research". Vaccine (2005) 23, 2243-50.

Bojang K. A., Olodude, F., Pinder, M., Ofori-Anyinam, O., Vigneron, L., Fitzpatrick, S., Njie, F., Kassanga, A., Leach, A., Milman, J., Rabinovich, R., McAdam, K. P., Kester, K. E., Heppner, D. G., Cohen, J. D., Tornieporth, N., and Milligan, P. J.: "Safety and immunogenicity of RTS,S/AS02A Candidate Malaria Vaccine in Gambian Children". Vaccine (2005) 23 (32), 4148-4157.

Pedro L Alonso, Jahit Sacarlal,John J Aponte,Amanda Leach, Eusebio Macete, Pedro Aide, Betuel Sigauque, Jessica Milman, Inacio Mandomando, Quique Bassat, Caterina Guinovart, Mateu Espasa, Sabine Corachan, Marc Lievens, Margarita M Navia, Marie-Claude Dubois, Clara Menendez, Filip Dubovsky, Joe Cohen, Ricardo Thompson, W Ripley Ballou: "Duration of protection with RTS,S/AS02A malaria vaccine in prevention of *Plasmodium falciparum* disease in Mozambican children: single-blind extended follow-up of a randomized controlled trial". The Lancet (2005) 366, 2012-18.

Susanna J. Dunachie, Michael Walther, Jenni M. Vuola , Daniel P. Webster, Sheila M. Keating, Tamara Berthoud, Laura Andrews, Philip Bejon, Ian Poulton, Geoffrey Butcher, Katherine Watkins, Robert E. Sinden, Amanda Leach, Philippe Moris, Nadia Tornieporth, Joerg Schneider, Filip Dubovsky, Eveline Tierney, Jack Williams, D. Gray Heppner, Jr, Sarah C. Gilbert, Joe Cohen, Adrian V.S. Hill: "A clinical trial of prime-boost immunisation with the candidate malaria vaccines RTS,S/AS02A and MVA-CS ". Vaccines (2006) 24 (15), 2850-59.

José A. Stoute, D. Gray Heppner, Carl J. Mason, Joram Siangla, Malachi O. Opollo, Kent E. Kester, Laurence Vigneron, Gerald Voss, Michael J. Walter, Nadia Tornieporth, Joe D. Cohen, W. Ripley Ballou: "Phase 1 safety and immunogenicity trial of malaria vaccine RTS,S/AS02A in adults in a hyperendemic region of western Kenya". Am. J. Trop. Med. Hyg. (2006) 75 (1), 166-170.

Walsh DS, Gettayacamin M; Leitner WW, Lyon JA, Stewart VA, Marit G, Pichyangkul S, Gosi P, Tongtawe P; Kester KE, Holland CA, Kolodny N, Cohen J, Voss G, Ballou WR, Heppner DG: "Heterologous prime-boost immunization in rhesus macaques by two, optimally spacedparticle-mediated epidermal deliveries of *Plasmodium falciparum* circumsporozoite protein-encoding DNA, followed by intramuscular RTS,S/AS02A" Vaccine (2006) 24 (19), 4167-78.

Sonia Enosse, Carlota Dobano, Diana Quelhas, John J. Aponte, Marc Lievens, Amanda Leach, Jahit Sacarlal, Brian Greenwood, Jessica Milman, Filip Dubovsky, Joe Cohen, Ricardo Thompson, W. Ripley Ballou, Pedro L. Alonso, David J. Conway, Colin J. Sutherland: "RTS,S/AS02A Malaria Vaccine does not induce parasite CSP T Cell epitope selection and reduces multiplicity of infection". Plos Clinical Trials May 2006 (e5), 001-0010.

Ann Stewart, Douglas Walsh, Shannon McGrath, Kent Kester, James Cummings, Gerald Voss, Martine Delchambre, Nathalie Garcon, Joe Cohen, Gray Heppner: "Cutaneous delayed-type hypersensitivity (DTH) in a multi-formulation comparator trial of the anti-*falciparum* malaria vaccine candidate RTS,S in rhesus macaques". Vaccine (2006) 24 (42-43),6493-6502.

Ann Stewart, Shannon McGrath, Douglas Walsh, Stacey Davis, Aaron Hess, Lisa Ware, Kent Kester, James Cummings, Robert Burge, Gerald Voss, Martine Delchambre, Nathalie Garcon, Douglas Tang, Joe Cohen, Gray Heppner: "Pre-clinical evaluation of new adjuvant formulation to improve the immunogenicity of the malaria vaccine RTS,S/AS02A", Vaccine (2006) 24 (42-43), 6483-92.

Ann Stewart, Shannon McGrath, Patrice Dubois, Maria Pau, Pascal Mettens, Joseph Shott, Michelle Cobb, Robert Burge, David Larson, Lisa Ware, Marie-Ange Demoitie, Gerrit Weverling, Babak Bayat, Jerome Custers, Marie-Claude Dubois, Joe Cohen, Jaap Goudsmit, Gray Heppner: "Priming with an Adeonvirus 35-Circumsporozoite Protein (CS) vaccine followed by RTS,S/AS01B Boosting Significantly Improves Immunogenicity to *Plasmodium falciparum* CS compared to that with either Malaria vaccine alone". Infection & Immunity (2007) 75 (5), 2283-2290.

E. Macete, J.J. Aponte, C. Guinovart, H. Sacarlal, O. Ofori-Anyinam, I. Mandomando, M. Espasa, C. Bevilacqua, A. Leach, MC. Dubois, D.G. Heppner, L. Tello, J, Milman, J. Cohen, F. Dubovsky, N. Tornieporth, R. Thompson, P. Alonso: "Safety and Immunogenicity of the RTS,S/AS02A candidate malaria vaccine in children aged 1-4 in Mozambique". Tropical Medicine & International Health (2007) 12 (1), 37-46.

Ken Kester, Denise McKinney, Nadia Tornieporth, Christian Ockenhouse, Gray Heppner, Ted Hall, Bruce Wellde, Kate White, Peifang Sun, Robert Schwenk, Urszula Krzych, Martine Delchambre, Gerald Voss, Marie-Claude Dubois, Robert Grasser, Megan Dowler, Megan O'Brien, Janet Wittes, Robert Wirtz, Joe

(56) References Cited

OTHER PUBLICATIONS

Cohen, Ripley Ballou: "A phase I/IIa safety, immunogenicity, and efficacy bridging randomized study of a two-dose regimen of liquid and lyophilized formulations of the candidate malaria vaccine RTS,S/AS02A in malaria-naïve adults". Vaccine (2007) 25 (29), 5359-5366.

Eusebio Macete, Jahit Sacarlal, John Aponte, Amanda Leach, Margarita Navia, Jessica Milman, Caterina Guinovart, Inacio Mandomando, Yolanda Lopez-Pua, Marc Lievens, Alex Owusu, Marie-Claude Dubois, Conor Cahill, Marguerite Koutsoukos, Marla Sillman, Ricardo Thompson, Filip Dubovsky, Ripley Ballou, Joe Cohen, Pedro Alonso: "Evaluation of two formulations of adjuvanted RTS,S malaria vaccine in children aged 3 to 5 years living in a malaria-endemic region of Mozambique: a Phase I/IIb randomized double-blind bridging trial", Trials (2007) 8, 11.

John Aponte, Pedro Aide, Montse, Renom, Inacio Mandomando, Quique Bassat, Jahit Sacarlal, Nelia Manaca, Sarah Lafuente, Arnold Babosa, Amanda Leach, Marc Lievens, Johan Vekemans, Betuel Sigauque, Marie-Claude Dubois, Marie-Ange Demoitie, Marla Sillman. Barbara Savarese, John McNeil, Eusebio Macete, Ripley Ballou, Joe Cohen, Pedro Alonso: "Safety of the RTS,S/AS02D candidate malaria vaccine in infants living in a highly endemic area of Mozambique: a double blind randomized controlled phase I/IIb trial". Lancet (2007) 370, 1543-1551.

Jahit Sacarlal, John Aponte, Pedro Aide, Inacio Mandomando, Quique Bassat, Caterina Guinovart, Amanda Leach, Jessica Milman, Eusebio Macete, Mateu Espasa, Opokua Ofori-Anyinam, Joelle Thonnard, Filip Dubovsky, Ripley Ballou, Joe Cohen, Pedro Alonso: "Safety of the RTS,S/AS02A malaria vaccine in Mozambican children during a phase IIb trial". Vaccine (2008) 26, 174-184.

Kent Kester, James Cummings, Christian Ockenhouse, Robin Nielsen, Ted Hall, Daniel Gordon, Robert Schwenk, Urszula Krzych, Carolyn Holland, Gregory Richmond, Megan Dowler, Jackie Williams, Robert Wirtz, Nadia Tornieporth, Laurence Vigneron, Martine Delchambre, Marie-Ange Demoitie, Ripley Ballou, Joe Cohen, Gray Heppner: "Phase 2a trial of 0, 1 and 3 month and 0, 7 and 28 day immunization schedules of malaria vaccine RTS,S/AS02 in malaria-naïve adults at the Walter Reed Army Institute of Research". Vaccines (2008) 26, 2191-2202.

Mettens Pascal, Dubois Patrice, Demoitie Marie-Ange, Bayat Babak, Donner Marie-Noëlle, Bourguignon Patricia, Stewart Ann, Heppner Gray, Garcon Nathalie, Cohen Joe: "Improved T cell responses to *Plasmodium falcibarum* circumsporozoite protein in mice and monkeys induced by a novel formulation of RTS,S vaccine antigen". Vaccine (2008) 26, 1072-1082.

Bejon P, Lusingu J. Olotu A, Leach A, Lievens M, Vekemans J, Mshamu S, Lang T, Gould J, Dubois MC, Demoite MA, Stallaert JF, Vansadia P, Carter T, Njuguna P, Awuondo K, Malabeja A, Abdul O, Gesase S, Mturi N, Drakeley C, Savarese B, Villafana T, Ballou R, Cohen J, Riley E, Lemnge M, Marsh K, Von Seidlein L: "Efficacy of RTS,S/AS01E Vaccine against Malaria in Children 5 to 17 months of age", NEJM (2008), 359, 24; 2521-32.

Adbulla S, Oberholzer R; Juma O, Kubhoja S, Machera F, Membi C, Omari S, Urassa A, Mshinda H, Jumanne A, Salim N, Shomari M, Aebi T, Schellenberg D, Carter T, Villafana T, Demoitie MA, Dubois MC, Leach A, Lievens M, Vekemans J, Cohen J, Ballou R, Tanner M: Safety and Immunogenicity of RTS,S/AS02D Maiaria Vaccine in Infants. NEJM (2008) 359, 24: 2533-44.

Pichyangkul S, Kum-Arb U, Yongvanitchit K, Limsalakpetch A, Gettayacamin M, Lanar D E, Ware L A, Stewart V A, Heppner D G, Mettens P, Cohen J D, Ballou W R, Fukuda M M: "Preclinical evaluation of the safety and immunogenicity of a vaccine consisting of *Plasmodium falciparum* liver-stage antigen 1 with adjuvant AS01B administered alone or concurrently with the RTS,S/AS01B vaccine in rhesus primates". Infection and immunity 2008;76(1)229-38.

Bojang K, Milligan F, Pinder M, Doherty T, Leach A, Ofori-Anyinam O, Lievens M, Kester K, Schaecher K, Ballou R, Cohen J.: "Five year safety and immunogenicity of GlaxoSmithKline's candidate malaria vaccine RTS,S/AS02 following administration to semi-immune adult men living in a malaria-endemic region of The Gambia". Hum Vaccines (2009) 5 (4), 1-6.

Guinovart C; Aponte J; Sacarlal J; Aide P; Leach A; Bassat Q; Macete E; Dobano C; Lievens M; Loucq C; Ballou R; Cohen J; Alonso P.: "Insights into long-lasting protection induced by RTS,S/AS02A malaria vaccine: further results from a phase IIb trial in Mozambican children", PLoSONE (2009) 4 (4): e5165.

Kester K; Cummings J, Ofori-Anyinam O, Ockenhouse C; Krzych U, Moris P, Schwenk R; Nielsen R; Debebe Z, Pinelis E, Juompan L, Williams J, Dowler M, Stewart A, Wirtz R; Dubois MC, Lievens M, Cohen J; Ballou R; Heppner D and the RTS,S Vaccine Evaluation Group: "Randomized, double-blind, phase 2a Trial of *falciparum* malaria vaccines RTS,S/AS01B and RTS,S/AS02A in malaria-naive adults: safety, efficacy and immunologic associates of protection", JID (2009) 200; 337-346.

Sacarlal J, Aide P, Aponte J; Renom M; Leach A, Mandomando I, Lievens M, Bassat Q, Lafuente S, Macete E, Vekemans J, Guinovart C, Sigauque B, Sillman M, Milman J, Dubois MC, Demoitie MA, Thonnard J, Menendez C, Ballou R, Cohen J, Alonso P: "Long-term safely and efficacy of the RTS,S/AS02A malaria vaccine in Mozambican children". JID (2009) 200: 329-336.

Polhemus M; Remich S; Ogutu B; Waitumbi J; Otieno L; Apollo S; Cummings J; Kester K; Ockenhouse C; Stewart A; Ofori-Anyinam O; Ramboer I; Cahill C; Lievens M, Dubois MC; Demoitie MA; Leach A; Cohen J; Ballou R; Heppner G. "Evaluation of RTS,S/AS02A and RTS,S/AS01B in Adults in a High Malaria Transmission Area", 2009, PLoS 4 (7) e6465.

Owusu-Agyei S, Ansong D, Asante K, Kwarteng Owusu S, Owusu R, Ayiwa Wireko Brobby N, Dosoo D, Osei Akoto A, Osei-Kwakye K, Asafo Adjei E, Owusu Boahen K, Sylverken J, Adjei G, Sambian D, Apanga S, Kayan K, Vekemans J, Ofori-Anyinam O, Leach A, Lievens M, Demoitie MA, Dubois MC, Cohen J, Ballou WR, Savarese B, Chandramohan D, Owusu Gyapong J, Milligan, P Antwi S, Agbenyega T, Greenwood B, Evans J: "Randomized Controlled Trial of RTS,S/AS02D and RTS,S/AS01E Malaria Candidate Vaccines Given According to Different Schedules in Ghanaian Children". 2009, PLoS 4 (10) e7302.

Cohen J: "Malaria vaccine Development: trials, tribulations and reasons for hope". 2009 Human vaccines 5-1 (2-5).

Lell B, Gnandji A, Von Glasenapp I, Haertle S, Oyakhiromen S, Issifou S, Vekemans J, Leach A, Lievens M, Dubois MC, Demoitie MA, Carter T, Villafana T. Ballou W, Cohen J, Kremsner P: "A Randomized Trial Assessing the Safety and Immunogenicity of AS01 and AS02 Adjuvanted RTS,S Malaria Vaccine Candidates in Children in Gabon"; 2009, PLoS 4 (10) e7611.

Waitumbi J, Anyona S, Hunja C, Kifude C, Polhemus M, Walsh O, Ockenhouse C; Heppner G, Leach A; Lievens M, Ballou R, Cohen J, Sutherland C: "Impact of RTS,S/AS02$_A$ and RTS,S/AS01$_B$ on Genotypes of *P. falciparum* in Adults Participating in a Malaria Vaccine Clinical Trial", 2009, PLoS 4 (11)e7849.

Vekemans J, Leach A, Cohen J: "Development of the RTS,S/AS malaria candidate vaccine." 2009 Vaccine 27S: G67-71.

Pichyangkul S, Tongtawe P., Kum-Arb U, Yongvanitchit K, Gettayacamin M; Hollingdale MR, Limsalakpetch A; Stewart A, Lanar D, Dutta S, Angov E; Ware LA, Bergmann-Leitner E; House B; Voss G; Dubois MC, Cohen J, Fukuda M, Heppener D, Miller R.: "Evaluation of the safety and immunogenicity of *Plasmodium falciparum* apical membrane antigen 1, merozoite surface protein 1 or RTS,S vaccines with adjuvant system AS02$_A$ administered alone or concurrently in rhesus monkeys". 2009 Vaccine 28; 452-462.

Cohen J, Nussenzweig V, Nussenzweig R, Vekemans J, Leach A.: "From the circumsporozoite protein to the RTS,S/AS candidate vaccine", 2010 Human Vaccines 6 (1): 1-7.

Vahey M., Wang Z, Kester K, Cummings. J; Heppner G; Nau M; Ofori-Anyinam O; Cohen J; Coche T: Ballou R; Ockenhouse C.; "Expression of Genes Associated with Immunoproteasome Processing of Major Histocompatibility Complex Peptides Is indicative of Protection with Adjuvanted RTS,S Malaria Vaccine". 2010 JID 201: 580-589.

Agnandji ST, Asante KP, Lyimo J, Vekemans J, Soulanoudjingar SS, Owusu R, Shomari M, Leach A, Fernandes J, Dosoo D, Chikawe M, Issifou S, Osei-Kwakye K, Lievens M, Paricek M, Apanga S,

(56) References Cited

OTHER PUBLICATIONS

Mwangoka G, Okissi B, Kwara E, Minja R, Lange J, Boahen O, Kayan K, Adjei G, Chandramohan D, Jongert E, Demoitié MA, Dubois MC, Carter T, Vansadia P, Villafana T, Sillman M, Savarese B, Lapierre D, Ballou WR, Greenwood B, Tanner M, Cohen J, Kremsner PG, Lell B, Owusu-Agyei S, Abdulla S. : "Evaluation of the safety and immunogenicity of the RTS,S/AS01E malaria candidate vaccine when integrated in the expanded program of immunization" 2010 J infect Dis 202(7): 1076-87.

Aide P, Aponte J, Renom M, Nhampossa T, Sacarlal J, Mandomando I, Bassat Q, Manaca MN, Leach A, Lievens M, Vekemans J, Dubois MC, Loucq C, Ballou R, Cohen J, Alonso P: "Safety, immunogenicity and direction of protection of the RTS,S/AS02$_D$ Malaria vaccine: one year follow-up of a randomized controlled phase I/IIb Trial", 2010 PLoS One 5 (11): e13838.

Cohen J, Benns S, Vekemans J, Leach A: "Le candidat vaccine antipaludique RTS,S/AS est entré en essais cliniques de phase III". 2010 Annales Pharmaceutiques Françaises 68 : 370-9.

J. Lusingu, A. Olotu, A. Leach, M. Lievens, J. Vekemans, A. Olivier, S. Beens, R. Olomi, S. Msham, T. Lang, J. Gould, K. Hallez, Y. Guerra, P. Njuguna, K. Awuondo, A. Malabeja, O. Abdul S. Gesase, D. Dekker, L. Malle, S. Ismael, N. Mturi; C. Drakeley, B. Savarese, T. Villafana, R. Ballou, J. Cohen, E. Riley, M. Lemnge, K. Marsh, P, Bejon, L. Von Seidling: "Safety on the Malaria Vaccine Candidate, RTS,S/AS01E in 5 to 17 month old Kenyan and Tanzanian children". 2010 PLoS One 5 (11): e14090.

A. Olotu, A Leach, M. Lievens, J. Vekemans, S. Msham, T. Lang, J Gould, MC Dubois, E. Jongert, P. Vansadia, T. Carter, P. Njuguna, K. Awuondo, A. Malabeja, O. Abdul, S Gesase, N Mturi, C. Drakeley B. Savarese, T. Villafana, D Lapierre, R Ballou, J Cohen, M. Lemnge, N Peshu, K Marsh, E. Riley, L. Seidlei, P. Bejon: "Efficacy of RTS,S/AS01E malaria vaccine and exploratory analysis on anti-circumsporozoite antibody titres and protection in children aged 5-17 months in Kenya and Tanzania: a randomised controlled trial". 2011 Lancet Infect Dis 11: 102-109.

P. Aide, C. Dobano, J. Sacarlal, J Aponte, I. Mandomando, C. Guinovart, Q. Bassat, M. Renom, L. Puyol, E. Macete, E. Herreros, A. Leach, MC. Dubois, MA. Demoitie, M. Lievens, J. Vekemans, C. Loucq, R. Ballou, J. Cohen, P. Alonson : << Four year immunogenicity of the RTS,S/AS02$_A$ malaria vaccine in Mozambican children during a phase IIb trial. 2011 Vaccine 29 (35): 6059-6067.

P. Bejon, J Cook, E. Bergmann-Leitner, A. Olotu, J. Lusingu, J Mwacharo, J Vekemans, P Njuguna, A. Leach, M Lievens, S Dutta, L Von Seidlein, B Savarese, T Villafana, MM Lemnge, J Cohen, K Marsh, PH. Corran, E Angov, E Riley, and C. Drakeley: "Effect of the Pre-erythrocytic Candidate Malaria Vaccine RTS,S/AS01E on Blood Stage Immunity in Young Children". 2011 JID (204): 9-18.

S. Agnandji, R. Fendel, M. Mestre, M Janssens, J. Vekemans, J. Held, F Gnansounou, S. Haertle, I Von Glasenapp, S. Ayakhirome, L. Mewono, P. Moris, M. Lievens, MA Demoitie, P. Dubois, T. Villafana, E, Jongert, A. Olivier, J. Cohen, M. Esen, P. Kremsner, B. Lell, B. Mordmuller: "Induction of *Plasmodium faiciparum*-Specific CD4$^+$ T cells and memory B cells in Gabonese children vaccinated with RTS,S/AS01$_E$ and RTS,S/AS02$_D$". 2011 PLoSOne 6 (4) e18559.

D. Ansong, K. Asante, J, Vekemans, S. Owusu, R. Owusu, N. Brobby, D. Dosoo, A. Osei-Koto, K. Osei-Kwakye, E. Asafo-Adjei, K. Boahen, J. Sylverken, G. Adjei, D. Sambian, S. Apanga, K. Kayan, M. Janssens, M. Lievens, A. Olivier, E. Jongert, P. Dubois, B. Savarese, J. Cohen, S. Antwi, B. Greenwood, J. Evans, T. Agbenyega, P. Moris, S. Owusu-Agyei "T Cell responses to the RTS,S/AS01$_E$ and RTS,S/AS02$_D$ malaria candidate vaccines administered according to different schedules to Ghanaian children". 2011 PLoSOne 6 (4) e18891.

KP. Asante, S. Abdulla, S. Agnandji, J Lyimo, J. Vekemans, S. Soulanoudjingar, R. Owusu, M. Shomari, A. Leach, E. Jongert, N. Salim, J. Fernandes, D. Dosoo, M. Chikawe, S. Issifou, K. Osei-Kwakye, M, Lievens, M. Paricek, T. Moller, S. Apanga, G. Mwangoka, MC. Dubois, T. Madi, E, Kwara, R. Minja, A. Hounkpatin, O. Boahen, K. Kayan, G. Adjei, D Chandramohan, T. Carter, P. Vansadia, M. Sillman, B. Savarese, C. Loucq, D. Lapierre, B. Greenwood, J. Cohen, P. Kremsner, S. Owusu-Agyei, M. Tanner, B. Lell: "Safety and efficacy of the RTS,S/AS01$_E$ candidate malaria vaccine given with expanded-programme-on-immunisation vaccines: 19 month follow-up of a randomised, open-label, phase 2 trial". 2011 Lancet Inf Dis 11: 741-49.

Cohen J, Beens S, Veekemans J, Leach A, Schuerman L.: "Development of the RTS,S/AS vaccine candidate from concept to Phase III". 2011 Progress in Parasitology—Parasitology Research Monographs 2: 121-133.

Lumsden J, Schwenk R, Rein L, Moris P, Janssens M, Ofori-Anyinam O, Cohen J, Kester K, Heppner G, Krzych U: "Protective immunity induced with the RTS,S/AS vaccine is associated with IL-2 and TNF-α producing effector and central memory CD4$^+$ T cells". 2011 PLoS One: 6 (7): e20775.

Olotu A, Moris P, Mwacharo J, Vekemans J; Kimani D, Janssens M, Kai O, Jongert E, Lievens M, Leach A, Villafana T, Savarese B, Marsh K, Cohen J, Bejon P: "Circumsporozoite-Specific T Cell Responses in Children Vaccinated with RTS,S/AS01$_E$ and Protection against *P. falciparum* Clinical Malaria". 2011 PLoS One 6 (10): e25786.

The RTS,S Clinical Trial Partnership: "First results of Phase 3 Trial of RTS,S/AS01 Malaria Vaccine in African Children". 2011 NEJM 365 (20); 1863-75.

Horowitz A, Hafalla JCR, King E, Lusingu J, Dekker D, Leach A, Moris P. , Cohen J, Vekemans J, Villafana T, Corran P, Bejon P, Drakeley C, Von Seidlein L, Riley E: "Antigen-Specific IL-2 Secretion Correlates with NK Cell Responses after Immunization of Tanzanian Children with the RTS,S/AS01 Malaria Vaccine". 2012 J Immunol 188: 5054-62.

The RTS,S Clinical Trials Partnership: "A Phase 3 Trial of RTS,S/AS01 Malaria Vaccine in African Infants", N Engl J Med 2012. Doi: 10.1056/NEJMoa1208394.

Abdulla S, Salim N, Machera F, Kamata R, Juma O, Shomari M, Kubhoja S, Mohammed A, Mwangoka G, Aebi T, Mshinda H, Schellenberg D, Carter T, Villafana T, Dubois MC, Leach A, Lievens M, Vekemans J, Cohen J, Ballou R, Marcel Tanner M: "Randomized, controlled trial of the long term safety, immunogenicity and efficacy of RTS,S/AS02D malaria vaccine in infants living in a malaria-endemic region": Malar J . 2013; 12 (1): 11.

Stewart, V A; McGrath, S M I; Davis, S A; Manganello, L M; Kester, K E; Cohen, J: Voss, G; Heppner, D G., "Comparison of Three Novel Adjuvants and an Accelerated Administration Schedule in Rhesus Macaques for Optimizing of the RTS, S Anti-Falciparum Malaria Vaccine Candidate", abstract, The American journal of tropical medicine and hygiene, 65:232. Nov. 13, 2001.

Holland, CA; Williams, J; Heppner, DG; Tornieporth, N; Vigneron, L; Delchambre, M; Cohen, J; Kester, KE, "Humoral immune responses in recipients of RTS, S/AS02 when given in two short course schedules", abstract. The American journal of tropical medicine and hygiene, 65:232. Nov. 13, 2001.

McGrath, SM; Davis, S A; Manganello, I M; Kester, K E; Voss, G; Cohen, J; Heppner, D G; Stewart, V A, "Use of The Elispot Assay In Rhesus Macaques for Optimizing of the RTS, S Malaria Vaccine Candidate With New Adjuvant Formulations", abstract, American Society of Tropical Medicine and Hygiene, 65:242. Nov. 13, 2001.

Holland CA Williams J, Heppner DG, Tornieporth N, Vigneron L Delchambre M, Wirtz RA, Cohen J, Kester KE "Humoral immune responses in recipients of rts, s/as02 when given in two short course schedules" poster Nov. 13, 2001.

Kester, Kent E, "Safety, Immunogenicity, And Preliminary Efficacy of Two Short Courses Schedules of RTS/As02" Nov. 13, 2001.

V. Ann Stewart, "Optimization of the anti-falciparum malaria vaccine candidate RTS, S in the rhesus macaque" presentation (associated with 1c above) Nov. 13, 2001.

The work or data disclosed at the Fourth Meeting on Novel Adjuvants in/close to Human Clinical Testing, sponsored by the WHO, Annecy, France, Jun. 23-25, 2003. (2a-2c).

Dubois, P.; Stewart, A., "Induction of antigen specific CD4 and CD8 T cell responses after vaccination with proteins combined to adjuvant" Jun. 23-25, 2003.

Folasade Olodude & Eusebio Macete, MRC, Gambia & CSIM, Mozambique, "Preliminary assessment of the safety and

(56) References Cited

OTHER PUBLICATIONS immunogenicity of the RTS, S/AS02A malaria vaccine candidate in 1-11 year old childern". Jun. 23-25, 2003.
Meeting agenda Jun. 23-25, 2003.
The work or data disclosed in the Abstracts of the 4th Multilateral Initiative in Malaria Meeting, Yaounde, Cameroon, Nov. 13-18, 2005 (3a through 3i below).
Wootton, D; Opara, H; Dube-mbeye, Q; Kanjala, M; Neate, C; Kirby, P; Milligan, P; Molyneux, M; Dunyo, S; Winstanley, P, "A dose-ranging, phase II trial of chlorproguanil-dapsone with 3 doses of artesunate for the treatment of acute uncomplicated P. falciparum malaria" Nov. 13-18, 2005.
Sah, S; South, R; Ali, R; Kebede, F, "Behaviour change for improved malaria prevention and treatment in White Nile State (WNS), Sudan". Nov. 13-18, 2005.
Bruegge, E; Dunford, C; Gray, B; Davis, R; South, R; Armarklemesu, M; Dearden, K, "Microfinance Against Malaria". Nov. 13-18, 2005.
Thera, M; Doumbo, O; Coulibaly, D; Diallo, D; Sagara, I; Heppner, G; Soisson, L; Leach, A; Lyke, K; Plowe, C, "Safety and Immunogenicity of the WRAIR and GSK Biologicals' Malaria Vaccine Candidate AMA-1/AS02A vs. Rabies Vaccine in Adults in Bandiagara, Mali" Nov. 13-18, 2005.
White, C; Kilian, A; Rwakimari, J; Bell, A; Mukasa, V; South, R, "Supporting national community health schemes: initial lessons for the Uganda malaria partnership programme". Nov. 13-18, 2005.
Haaland, A; Kachur, P; Kombe, F; Yaa, F; Barongo, V; Duparc, S; Marsh, V, "Visual Instructions promote malaria treatment". Nov. 13-18, 2005.
Cohen, J; Alonso, P.L.; Heppner, G.; Ballou, W.R.; Moree, M, "Malaria Vaccines: Not a dream any more". Nov. 13-18, 2005.
Cohen, J; Alonso, P.L.; Heppner, G.; Ballou, W.R.; Moree, M., "The RTS,S malaria vaccine: status and future plans". Nov. 13-18, 2005.
The work or data disclosed in the Abstracts of the 54th Meeting of the American Society of Tropical Medicine and Hygiene, Washington, DC, Dec. 11-15, 2005. (4a through 4l).
Angov, Evelina, Brent-Kirk, Afiya; Bowden, Scott A; Soisson, Lorraine A; Stoute, Jose A; Ockenhouse, Christian F; Cohen, Joe; Diggs, Carter L; Heppner, Donald G(; Lyon, Jeffrey A, "Analysis of antibody specificities detected by an MSP1-42 fragment specific ELISA following vaccination with FMP1/AS02A in three diverse populations". Dec. 11-15, 2005.
Angov, Evelina [Reprint Author]; Khan, Farhat; N-Leitner, Elke S. Bergman; Kincaid, Randall; Heppner, Donald G.; Soisson, Lorraine; Cohen, Joe; Diggs, Carter L.; Lyon, Jeffrey A., "Antibodies raised against Plasmodium falciparum MSP1-42 expressed from a fully codon-harmonized gene are significantly more growth inhibitory than those raised against the same antigen expressed from a partially codon-harmonized gene". Dec. 11-15, 2005.
Kester, Kent E.; Ockenhouse, Chris F.; Krzych, U.; Hall, B.T.; Stewart, V.A.; Williams, J.; Nielsen, R.; Polhemus, M.; Cummings, J.F.; Moran, K.; Magill, A. J.; Moris, P.; Ofori-Anyinam, O.; Dubois, M-C; Garcon, N.; Hanon, E.; Koutsokoukos, M.; Van Mechelen, M.; De Kock, E.; Dehottay, P.; Lievens, M.; Fourneau, M.; Ripley Ballou, W.; Cohen, Joe; Heppner, D. Gray, "Evaluation of a New Formulation of Glaxosmithkline's Candidate Malaria Vaccine RTS,S in the Novel Adjuvant AS01B: Safety, Immunogenicity, and Preliminary Efficacy". Dec. 11-15, 2005.
Shott, Joseph; Pau, Maria Grazia; DemoitiÃ ©, Marie-Ange; Custers, Jerome H.; McGrath, Shannon; Dubois, Patrice; Ophorst, Olga; Dubois, Marie Claude; Komisar, Jack; Cohen, Joe; Goudsmit, Jaap; Heppner, D. Gray; Stewart, V. Ann, "Evaluation of Immunogenicity of Adenovirus-PfCS Malaria Vaccine Candidates In Mice". Dec. 11-15, 2005.
Walsh, Douglas S.; Gettayacamin, Montip; Lyon, Jeffrey A.; Leitner, Wolfgang W.; Stewart, Ann; Pichyangkul, Sathit; Gosi, Panita; Tongtawe, Pongsir; Holland, Carolyn A.; Kolodny, Nelly; Cohen, Joe; Voss, Gerald, Ballou, Ripley; Heppner, D. Gray, Jr, "Heterologous prime-boost immunization with epidermal gene gun administered Plasmodium falciparum circumsporozoite protein (CSP) encoding DNA and instramuscular RTS,S/AS02A in rhesus monkeys generates robust cutaneous delayed-type hypersensitivity response against CSP C terminus". Dec. 11-15, 2005.
Stewart, V. Ann; McGrath, Shannon M.; Grazia Pau, Maria; Mettens, Pascal; Dubois, Patrice; Custers, Jerome H. H. V.; DemoitiÃ ©; Marie-Ange; Ophorst, Olga; Shott, Joseph; Bayat, Babak; Donner, Marie-NoÃ<<lle; Dubois, Marie-Claude; Goudsmit, Jaap; Cohen, Joe; Heppner, D. Gray, "Heterologous prime-boost with adenovirus35-vectored CS and recombinant protein RTS,S/AS01B greatly enhances immune responses to P. falciparum CS". Dec. 11-15, 2005.
Cobb, Michelle; McGrath, Shannon; Mutts, Sheetij; Ware, Lisa A.; Lalithe, P.V.; Cohen, Joe: Lanar, David E.; Heppner, D. Gray; Stewart, V. Ann, "Interferon-gamma ELISpot responses to PfAMA-1/E, a recombinant protein blood-stage P. falciparum vaccine candidate, in rhesus macaques". Dec. 11-15, 2005.
McGrath, Shannon M.; Bayat, Babak; Donner, Marie-NoÃ<<lle; Mettens, Pascal; Collignon, Catherine; Grazia Pau, Maria; Dubois, Patrice; Goudsmit, Jaap; Cohen, Joe; Heppner, D. Gray; Stewart. V. Ann, "Use of 6-color flow cytometry to measure immune response in rhesus macaques immunized with malaria candidates". Dec. 11-15, 2005.
The following publications or posters, slides and/or handouts therefrom: Koster KE. Malaria-027 trial results. WRAIR sponsored satellite presentation at ASTMH Philadelphia USA Dec. 11-15, 2005.
Kester, Kent E., "MAL-027: A Phase I/IIa Trial of RTS,S/AS01B vs. RTS,S/AS02A in Adults at the Walter Reed Army Institute of Research", Dec. 11-15, 2005.
The following publications or posters, slides and/or handouts therefrom:Polhemus ME. MAL 044 phase IIb clinical trial comparing two GSK adjuvant formulations AS01B and AS02A at the Walter Reed Project, Kisumu, Kenya. WRAIR sponsored satellite presentation at ASTMH Atlanta GA USA, Nov. 13-18, 2006.
ASTMH 55th Annual Meeting book Nov. 12-16 2006, Atlanta, GA.
52nd Annual Meeting and Centennial Celebration of the American Society of Tropical Medicine and Hygiene (ASTMH), Dec. 3, 2003, Philadelphia, PA; USA.
Bojang, KA; Olodude, F; Milligan, P; Pinder, M; Vigneron, L; Leach, A; Chilengi, R; Bevilacqua, C; Ofori-Anyinam, O; Fitzpatrick, S; Milman, J; McAdam, KPWJ; Rabinovich, R; Cohen, J; Tornieporth, N, "Safety and Immunogenicity of RTS,S/AS02A Malaria Vaccine in Gambian Children", Abstract. Dec. 3, 2003.
Cohen, J., Development of RTS, S: The Plasmodium Falciparum Recombinant CS Protein Vaccine Dec. 3, 2003, No Abstract provided either online or in Abstract book—part of a special symposium so may not be published,
Cohen J. D., "The RTS, S/AS02A Malaria Vaccine Candidate" Dec. 3, 2003, No Abstract provided either online or in Abstract book.
Vaccines of the Future: From Rational Design to Clinical Development, Oct. 17, 2001, Paris; France.
Cohen. J.D., "Malaria Vaccine Development: a Status Report" Oct. 17, 2001 No Abstract provided.
Vaccines 3: Frontiers in Vaccine Development, Oct. 7, 2004, Paris; France.
Cohen, Joe, Recent Advances in Malaria Vaccine Development presentation. Abstract. Oct. 7, 2004.
11th International Congress of Immunology, Jul. 22, 2001, Stockholm; Sweden.
Sun, P; Schwenk, R: Heppner, D G; Krzych, U; Cohen, J. "The Involvement of P Falciparum Protein-Specific CD4+ and CD8+ T Cells in the Protective Immunity Induced by Candidate Malaria Vaccine, RTS,S" Abstract. Jul. 22, 2001.
48th Annual Meeting of the American Society of Tropical Medicine and Hygiene. Washington, D.C., USA. Nov. 28-Dec. 2, 1999. American Society of Tropical Medicine and Hygiene. Nov. 28, 1999.
Holland, C. A.; Williams, J.; Momin, P.; Delchambre, M.; Dubois, M. C.; Watson, E.; Mowery, K.; Tornieporth, N.; Vigneron, L.; Voss, G.; Cohen, J.; Ballou, W. R.; Kester, K. E., Department of Immunology, Walter Reed Army Institute of Research, Washington, DC, USA, American Journal of Tropical Medicine and Hygiene, (Sep. 1999) vol. 61, No. 3 Suppl., pp. 491. print. Meeting Info. Abstract.

(56) References Cited

OTHER PUBLICATIONS

20001231 Conference: ASTMH 49th Annual Meeting, Houston, Texas (USA), Oct. 29-Nov. 2, 2000. (World Meeting No. 000 5172) Organizer(s): American Society of Tropical Medicine and Hygiene.
Sun, PF; Schwenk, R; Palmer, D; Berenzon, D; Stoute, JA; Kester, KE; Cohen, J; Voss, G; Ballou, WR; Heppner, DG, "T lymphocytes responses induced by immunization with the candidate Plasmodium falciparum vaccine RTS, S/SBAS2" Am J Trop Med Hyg 2000; 62(3 Suppl.):200-01, Oct. 29, 2000, Houston, TX. Abstract.
Malaria: Functional Genomics to Biology to Medicine (C5), Feb. 28, 2006, Taos, NM.
Stewart, V. Ann; McGrath, Shannon; Shott, Joseph; Mettens, Pascal; Grazia Pau, Maria; DuBois, Patrice; Goudsmit, Jaap; Cohen, Joe; Heppner, D. Gray, "Heterologous prime-boost with adenovirus35-vectored CS and recombinant protein RTS,S/AS01 B greatly enhances immune responses to P. falciparum CS" Abstract. Feb. 28, 2006.
Ripley Ballou, W.; Cohen, Joe D., "Recent Progress with the RTS,S Malaria Vaccine", Malaria: Functional Genomics to Biology to Medicine (C5, Feb. 28, 2006, Taos, NM.) Abstract.
Aids Vaccine 2006, Aug. 29, 2006, Amsterdam, Netherlands.
Cohen, J, "Malaria: status of the field and the RTS,S vaccine as a case study" Abstract, Aug. 29, 2006.
2007 Malaria Vaccines for the World, Sep. 17, 2007, London, UK.
Stewart, V. Ann; McGrath, Shannon; Grazia Pau, Maria; Mettens, Pascal, Dubois, Patrice M.; Shott, Joseph; Demoiteé, Marie-Ange, Bayat, Babak; Donner, Marie-Noëlle; Dubois, Marie-Claude; Goudsmit, Jaap; Cohen, Joe; Gray Heppner, D., "Greatly enhanced immune responses from priming with Adenovirus35-CS followed by RTS,S/AS01B boost in rhesus macaques", Abstract Sep. 17, 2007.
56th Annual Meeting of the American Society of Tropical Medicine and Hygiene (ASTMH), Nov. 4, 2007, Phila, PA. (16a through 16h).
Aponte, John J.; Sacarlal, Jahit; Aide, Pedro; Macete, Eusebio; Renom, Montse; Bassat, Quique; Mandomando, Inacio; Manaca, Maria N.; Lafuente, Sarah; Leach, Amanda; Ballou, Ripley; Lievens, Marc; Thonnard, Joelle; Dubois, Marie-Claude; Demotie, Marie-Ange; Cohen, Joe; Dubovsky, Filip; Millman, Jessica; Sillman, Marla; Alonso, Pedro L., A 4 year follow-up of the safety, immunogenicity and efficacy of the candidate malaria vaccine RTS,S/AS02A in children vaccinated at aged 1 to 4 years in a malaria-endemic region of Mozambique. Abstract Nov. 4, 2007.
Aponte, John J.; Aide, Pedro; Renom, Montse; Mandomando, Inacio; Basset, Quique; Sacarlal, Jahit; Manaca, Maria N.; Lafuente, Sarah; Macete, Eusebio; Leach, Amanda; Ballou, Ripley; Lievens, Marc; Vekemans, Johan; Dubois, Marie-Claude; Demotie, Marie-Ange; Cohen, Joe; Dubovsky, Filip; Millman, Jessica; Sillman, Marla; Alonso, Pedro L., A Phase I/IIb randomized, double-blind, controlled clinical trial of the safety, immunogenicity and efficacy of RTS,S/AS02D, a candidate malaria vaccine in Mozambican infants. Abstract Nov. 4, 2007.
Lell, Bertand; Agnandji, Selidgi; von Glasenapp: Isabelle; Oyakhiromen, Sunny; Haertle, Sonja; Kremsner, Peter G.; Ramboer, Isabelle; Lievens, Marc; Ballou, Ripley; Vekemans, Johan; Dubois, Marie-Claude; Demoitie, Marie-Ange; Cohen, Joe; Villafana, Tonya; Carter, Terrell; Petersen, Carolyn, "A randomized, observer-blind trial to compare safety and immunogenicity of two adjuvanted RTS,S anti-malaria vaccine candidates in Gabonese children". Abstract Nov. 4, 2007.
Barbosa, Arnoldo; Naniche, Denise; Manaca, Maria N.; Aponte, John; Mandomando, Inacio; Aide, Pedro; Renom; Montse; Sacarlal, Jahit; Ballou, Ripley; Moris, Philippe; Cohen, Joe; Dubovsky, Filip; Millman, Jessica; Alonso, Pedro L., "Assessment of cellular immune responses in infants participating in a RTS,S/AS02D phase I/IIb trial in Mozambique", Abstract Nov. 4, 2007.
Barbosa, Arnoldo; Naniche, Denise; Manaca, Maria N.; Aponte, John; Mandomando, Inacio; Aide, Pedro; Renom; Montse; Sacarlal, Jahit; Ballou, Ripley; Moris, Philippe; Cohen, Joe; Dubovsky, Filip; Millman, Jessica; Alonso, Pedro L., "Assessment of cellular immune responses in infants participating in a RTS,S/AS02D phase I/IIb trial in Mozambique". Nov. 4, 2007.
Anyona, Samuel B.; Hunja, Carol W.; Kifude, Carolyne M.; Polhemus, Mark E.; Gray Heppner, D.; Leach, Amanda; Lievens, Marc; Ballou, Ripley; Cohen, Joe; Sutherland, Colin; Waitumbi, John N., "Impact of RTS,S/AS02A and RTS,S/AS01B on Multiplicity of Infections and CSP T-cell Epitopes of P. falciparum in Adults Participating in a Malaria Vaccine Clinical Trial". Abstract Nov. 4, 2007.
Pichyangkul, Sathit; Kum-Arb, Utaiwan; Yongvanitchit, Kosol; Limsalakpetch, Amporn; Gettayacamin, Monthip; Lanar, David E.; Ware, Lisa A.; Stewart, V. A.; Gray Heppner, D.; Mettens, Pascal; Cohen, Joe D.; Ballou, W. R.; Fukuda, Mark M., "Pre-clinical evaluation of safety and immunogenicity of Plasmodium falciparum LSA1/AS01B when administered separately or concurrently with RTS,S/AS01B in rhesus primates". Abstract Nov. 4, 2007.
Aponte, John J.; Sacarlal, Jahit, Aide, Pedro; Macete, Eusebio; Renom, Montse; Bassat, Quique; Mandomando, Inacio; Manaca, Maria N.; Lafuente, Sarah; Leach, Amanda; Ballou, Ripley; Lievens, Marc; Thonnard, Joelle; Dubois, Marie-Claude; Demotie, Marie-Ange; Cohen, Joe; Dubovsky, Filip; Millman, Jessica; Sillman, Marla; Alonso, Pedro L, "A Four-Year Follow-Up of the Safety, Immunogenicity and Efficacy of the Candidate Malaria Vaccine RTS,S/AS02A in Children Vaccinated at Aged 1 to 4 Years in a Malaria-Endemic Region of Mozambique". Abstract Nov. 4, 2007.
26th Annual Meeting of the European Society for Paediatric Infectious Diseases (ESPID), May 13, 2008, Graz, Austria.
von Glasenapp, I.; Lell, B.; Agnandji, S.; Oyakhiromen, S.; Haertle, S.; Kremsner, P.G.; Carter, T.; Sillman, M.; Villafana, T.; Lievens, M.; Vekemans, J.; Leach, A.; Dubois, M.C.; Demoitie, M.A.; Cohen, J.; Ballou, R., "AS01 and AS02 Adjuvanted RTS,S Anti-Malaria Vaccine Candidates: Safety and Immunogenicity in Children in Gabon". Abstract May 13, 2008.
2008 Malaria: Immunology, Pathogenesis and Vaccine Perspectives (E3)Jun. 8, 2008, Alpbach, Austria.
Cohen, Joe, "The RTS,S. Malaria Vaccine Candidate: From Phase II to Phase III" Abstract Jun. 8, 2008.
57th Annual Meeting of the American Society of Tropical Medicine and Hygiene (ASTMH) Dec. 7, 2008, New Orleans, LA.
Owusu-Agyei, Seth; Ansong, D.; Asante, K. P.; Owusu-Kwarteng, S.; Owusu, R.; Wireko Brobby, N. A.; Dosoo, D.; Osei Akoto, A. Y.; Osei-Kwakye, K.; Asafo Adjei, E.; Owusu Boahen, K.; Sylverken, J.; Adjei, G.; Sambian, D.; Vekemans, J.; Ofori-Anyinam, O.; Lievens, M.; Demoitie, M.; Cohen, J.; Ballou, W. R.; Savarese, B.; Greenwood, B.; Bawa, T.; Evans, J.; Agbenyega, T., "Phase II, Randomized Trial To Assess The Safety and Irnmunogenicity of The Candidate Malaria Vaccines RTS,S/AS02 and RTS,S/AS01 When Given According To Different Vaccination Schedules in Children in Ghana". Abstract Dec. 7, 2008.
Bejon, P.; Lusingu, J.; Olotu, Ally; Leach, A.; Lievens, M.; Vekemans, J.; Msham, S.; Lang, T.; Gould, J.; Dubois, M.C.; Demoitie, M.A.; Vansadia, P.; Carter, T.; Njuguna, P.; Kawuondo, K.; Gesase, S.; Drakeley, C.; Savarese, B.; Villafana, T.; Ballou, W. R Cohen, J.; Riley, E.; Lemnge, M.; Marsh, K.; von Seidlein, L., "Phase IIb, Randomized, Double-Blind Trial To Assess The Efficacy, Safety and immunogenicity of The Candidate Malaria Vaccine RTS,S/AS01 in Kenyan and Tanzanian Children", Abstract Dec. 7, 2008.
Abdulla, Salim; Oberholzer, R.; Juma, O.; Leach, A.; Vekemans, J.; Lievens, M.; Kuboja, S.; Salim, N.; Carter, T.; Demoitie, M.A.; Dubois, M.C.; Jurnanne, A.; Machel, F.; Membi, C.; Shomari, M.; Aebi, T.; Mshinda, H.; Villafana, T.; Cohen, J.; Ballou, W. R.; Tanner, M., "Phase IIb, Randomized, Double-Blind Trial To Assess The Safety, Immunogenicity and Efficacy of The Candidate Malaria Vaccine RTS,S/AS02 When Administered According To The Expanded Program on Immunization Schedule". Abstract Dec. 7, 2008.
6th European Congress on Tropical Medicine and International Health held jointly with the 1st Mediterranean Conference on Travel and Migration Medicine, Sep. 6, 2009, Verona, IT.
Cohen, J, "The vaccine RTS,S/AS: from the original insight to the development of the most promising candidate". Abstract Sep. 6, 2009.
3rd Annual Global Vaccine Congress, Oct. 4, 2009, Singapore, MY.
Cohen, J., "The RTS,S Malaria Vaccine candidate: Getting closer to the goal". Abatract Oct. 4, 2009.

(56) References Cited

OTHER PUBLICATIONS

5th Pan-African Conference of the Multilateral Initiative on Malaria (MIM), Nov. 2, 2009, Nairobi, Kenya.

Adnandji, Selidji T; Poku Asante, Kwaku; Lyimo, John; Vekemans, Johan; Soulanoudjingar, Solange S; Owusu, Ruth; Shomari, Mwanajaa; Leach, Amanda; Fernandes, Jose; Dosoo, David; Chikawe, Maria; Issifou, Saadou; Osei-Kwakye, Kingsley; Lievens, Marc; Paricek, Maria; Apanga, Stephen; Mwangoka, Grace; Dubois, Marie-Claude; Okissi, Blaise; Kwara, Evans; Minja, Rose; Lange, Jörn; Boahen, Owusu; Kayan, Kingsley; Adjei, George; Chandramohan, Daniel; Carter, Terrell; Vansadia, Preeti; Villafana, Tonya; Sillman, Marla; Savarese, Barbara; Lapierre, Didier; Greenwood, Brian; Tanner, Marcel; Cohen, Joe; Kremsner, Peter; Lell, Bertrand; Owusu Agyei, Seth; Abdulla, Salim, "Randomized, controlled Phase 2 study assessing the safety and immunogenicity of the RTS,S/AS01E candidate malaria vaccine, when incorporated into an EPI regimen including DTPwHepB/Hib, OPV, measles and yellow fever vaccination". Abstract Nov. 2, 2009.

58th Annual Meeting of the American Society of Tropical Medicine and Hygiene (ASTMH)Nov. 18, 2009 Washington, DC; USA.

Lumsden, Joanne; Schwenk, Robert J.; Egner, Lisa; Cohen, Joe; Ballou, Ripley; Ofori-Anyinam, Opokua; Moris, Philippe; Kester, Kent E.; Gray Heppner, D.; Krzych, Urszula, "IL-2-Producing Effector Memory and Central Memory CD4'T cell Subsets Are Associated with Protective Immunity in RTS,S-immunized Subjects". Abstract Nov. 18, 2009.

14th International Congress of Immunology (ICI)Aug. 22, 2010 Kobe; Japan.

Pichyangkul, S.; Tongtawe, P,; Kum-Arb, U.; Yongvanitchit, K.; Gettayacamin, M.; Hollingdale; M. R.; Limsalakpetch, A.; Heppner, D. G.; Cohen, J. D.; Bergmann-Leitner, E.S.; Ware, L. A.; Angov, E.; Dutta, S.; Lanar, D. E.; Stewart, V. A. Evaluation of the safety and immunogenicity of Plasmodium falciparum apical membrane antigen 1, merozoite surface protein 1 or RTS,S vaccines with adjuvant system $AS02_A$ administered alone or concurrently in rhesus monkeys. Abstract Aug. 22, 2010.

59th Annual Meeting of the American Society of Tropical Medicine and Hygiene (ASTMH) Nov. 3, 2010; Atlanta, GA; USA.

Asante, Kwaku Poku; Abdulla, Salim; Agnandji, Selidji; Lyimo, John; Vekemans, Johan; Soulanoudjingar, Solange; Owusu, Ruth; Shomari, Mwanajaa; Leech, Amanda; Salim, Nahya; Fernandes, Jose; Dosoo, David; Chikawe, Maria; Issifou, Saadou; Osei-Kwakye, Kingsley; Lievens, Marc; Paricek, Maria; Möller, Tina; Apanga, Stephen; Mwangoka, Grace; Dubois, Marie-Claude; Tigani, Madi; Okissi, Blaise; Kwara, Evans; Minja, Rose; Lange, Jorn; Houkpatin, Aurore; Boahen, Owusu; Kayan, Kingsley; Adjei, George; Chandramohan, Daniel; Carter, Terrell; Vansadia, Preeti; Sillman, Marla; Savarese, Barbara; Lapierre, Didler; Greenwood, Brian; Cohen, Joe; Kremsner, Peter; Agyei, Seth Owusu; Tanner, Marcel; Lell, Bertrand; Safety, immunogenicity and efficacy of the RTS, $S/AS01_E$ malaria vaccine candidate integrated in EPI: extended follow-up of a randomized controlled Phase 2 infant trial in Gabon, Ghana and Tanzania. Abstract Nov. 3, 2010.

Figure 1. Study design of primary efficacy endpoints
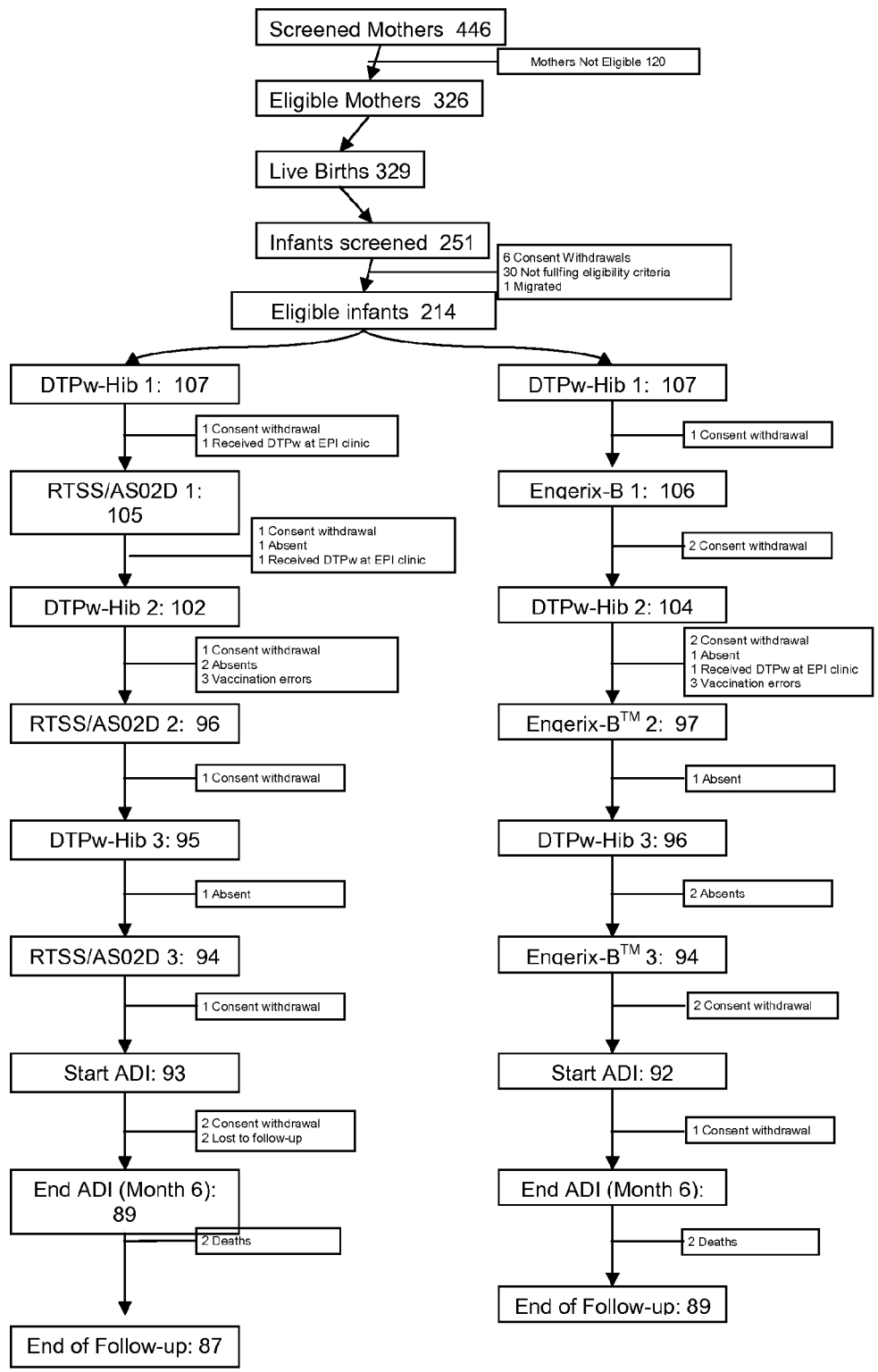

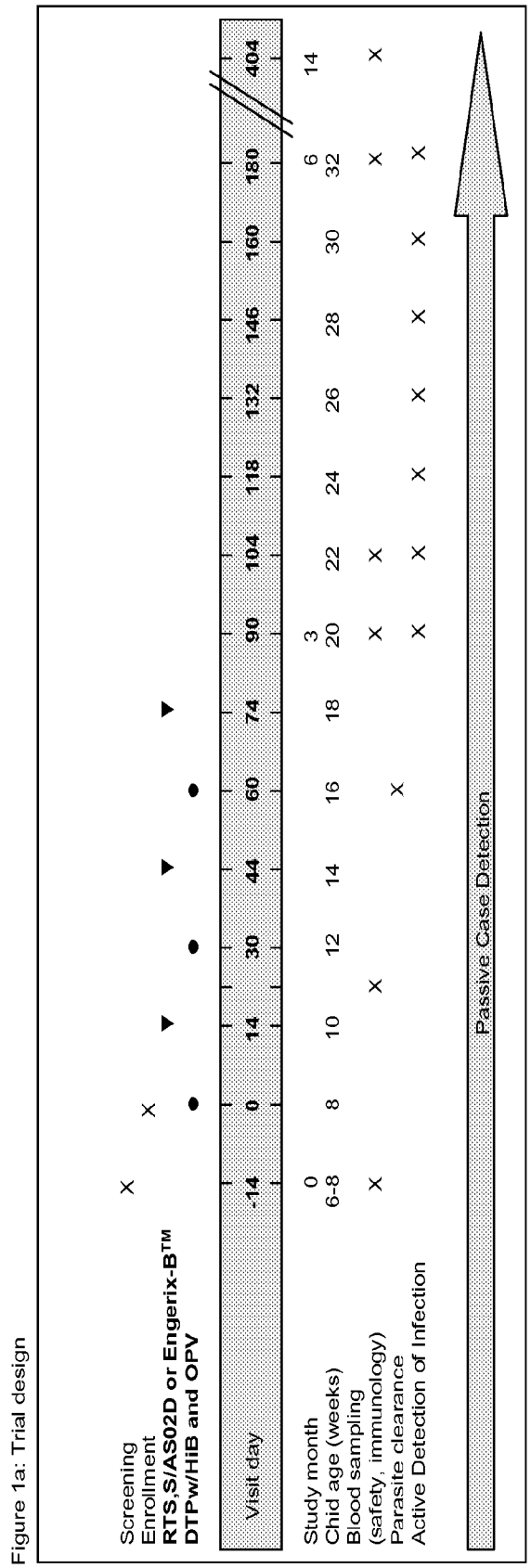
Figure 1a: Trial design

Reactogenicity data
The graphs below represent solicited systemic and local reactions following vaccination.
R stands for RTS,S
E stands for Engerix-B™.

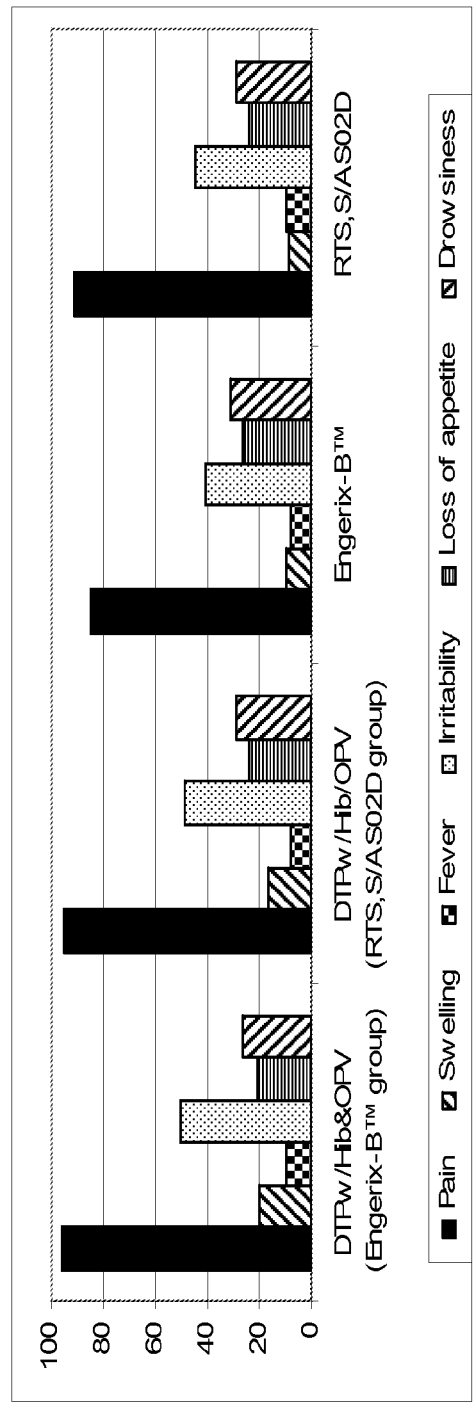
Figure 2c: Proportion of doses with solicited general symptoms reported during the 7 days post vaccination period

Figure 3

Efficacy

| | RTS,S/AS02D | | | | Engerix-B | | | | Point estimate of VE adjusted for covariates | | | Point estimate of VE unadjusted for covariates | | |
|---|---|---|---|---|---|---|---|---|---|---|---|---|---|---|
| | Subjects (N) | No. of events | PYAR | Rate | Subjects (N) | No. of events | PYAR | Rate | (%) | 95% CI | P value | (%) | 95% CI | P value |
| Infection [a] | 93 | 22 | 21.82 | 1.008 | 92 | 46 | 17.22 | 2.671 | 65.943 | 42.600 79.794 | <0.001 | 62.238 | 37.120 77.322 | <0.001 |
| Disease 1 [b] | 93 | 9 | 22.61 | 0.398 | 92 | 22 | 19.56 | 1.125 | 65.824 | 25.293 84.366 | 0.007 | 64.432 | 22.646 83.646 | 0.009 |
| Disease 2 [c] | 93 | 17 | 22.36 | 0.760 | 92 | 35 | 18.19 | 1.924 | 63.143 | 33.568 79.552 | <0.001 | 60.976 | 30.213 78.178 | 0.002 |
| Disease 3 [d] | 107 | 25 | 48.51 | 0.515 | 107 | 36 | 46.02 | 0.782 | 38.798 | -2.215 63.355 | 0.061 | 35.475 | -7.535 61.282 | 0.093 |

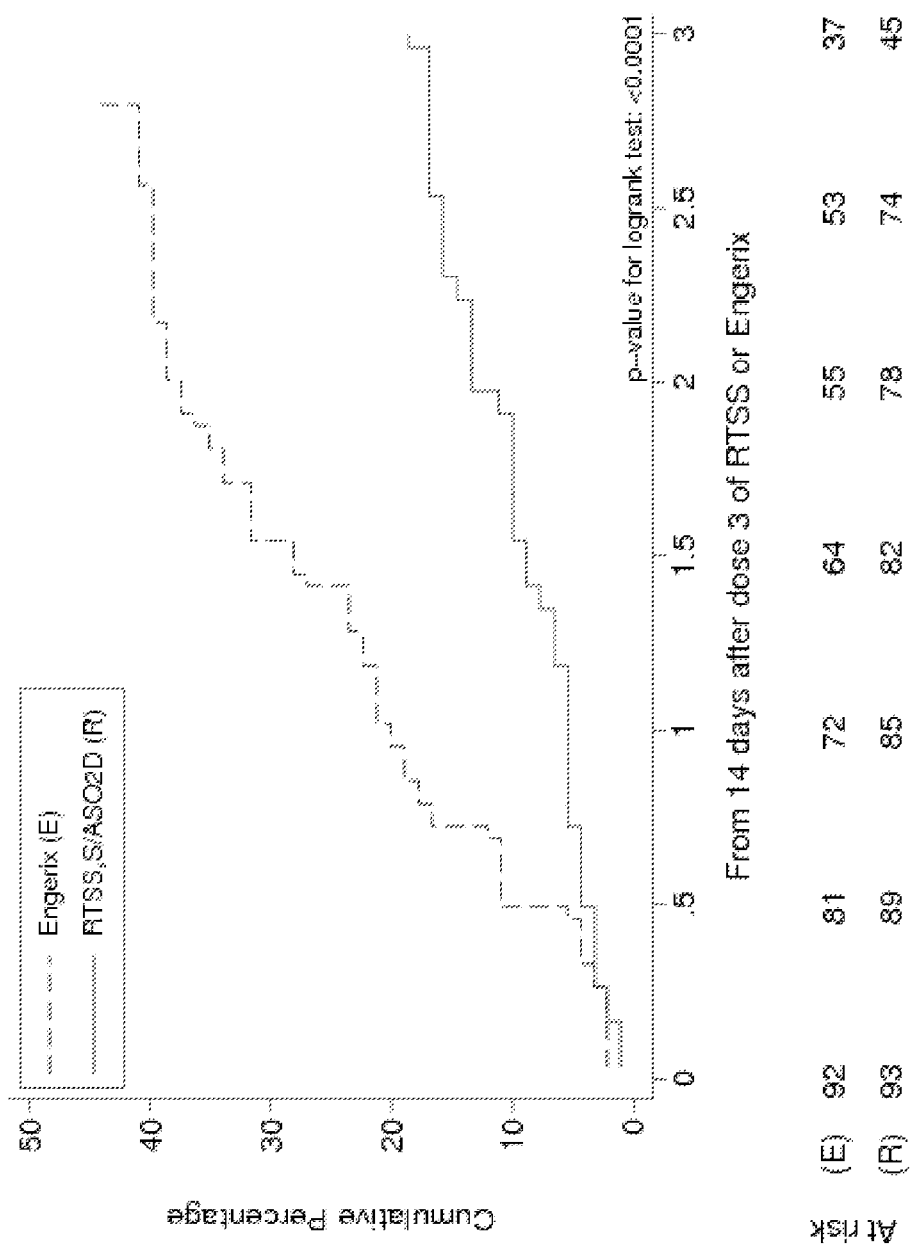
Figure 4: Kaplan-Meier curves for cumulative proportion with at least one episode of malaria infection from 038 trial

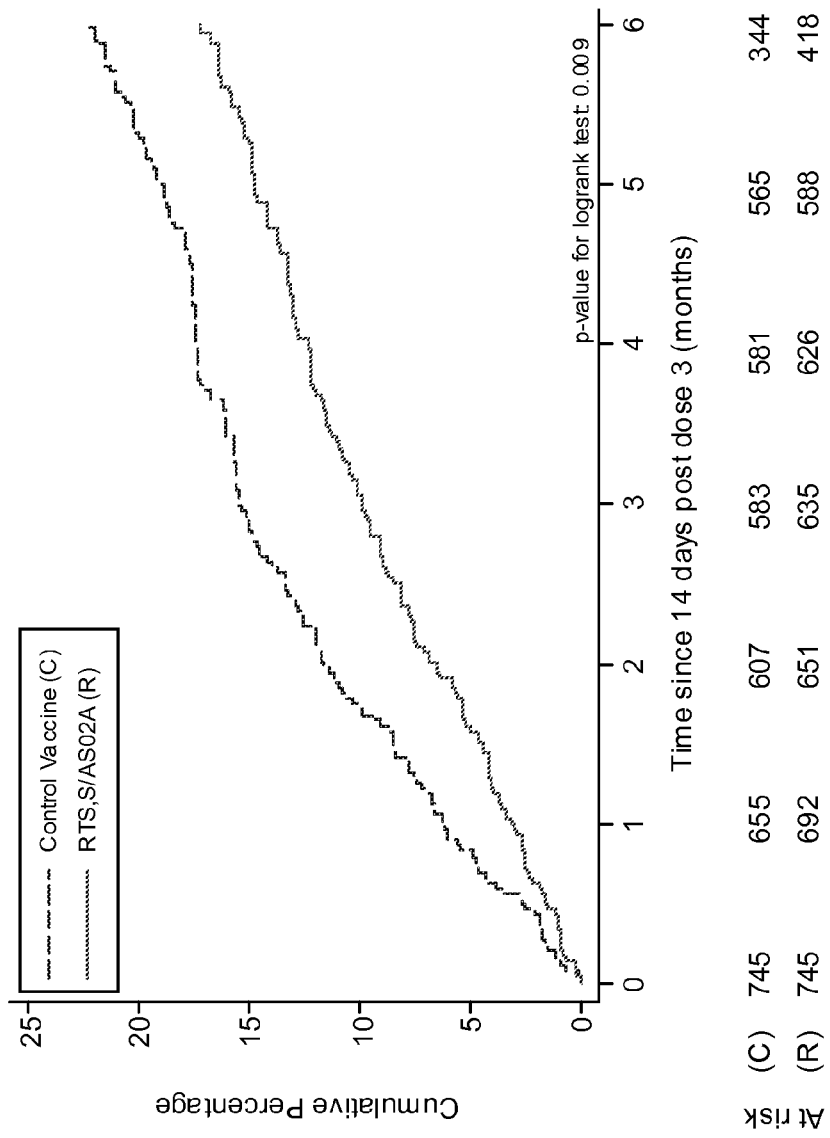
Figure 5a. Kaplan-Meier curve for the proportion of children with at least one episode of clinical malaria from the 026 study (children 1-4 in Mozambique)

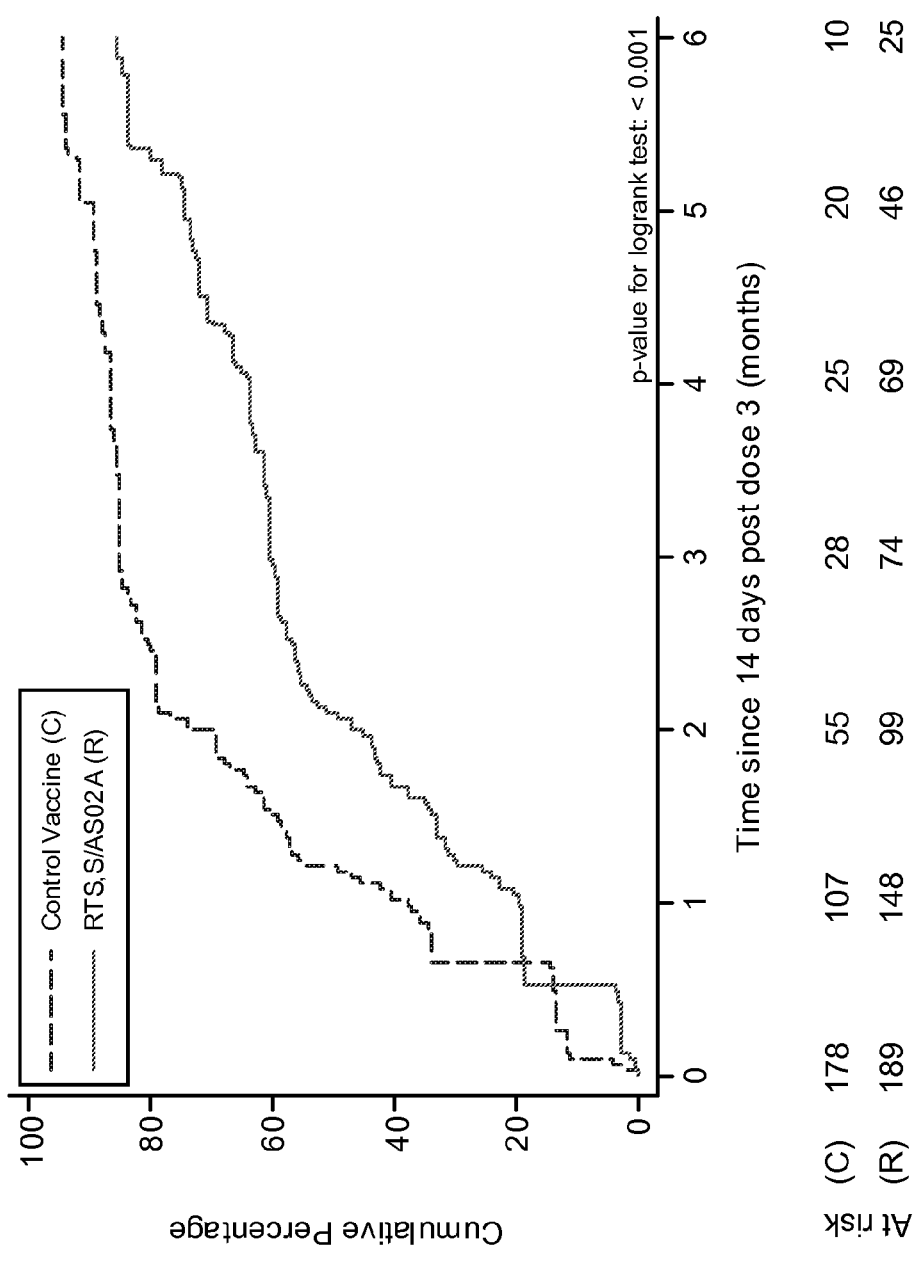

VACCINES

This application is the US National Stage of International Application No. PCT/EP2008/060505, filed 11 Aug. 2008, which claims benefit of the filing dates of U.S. Provisional Applications No. 60/955,445, filed 13 Aug. 2007, No. 60/957,338, filed 22 Aug. 2007, and No. 60/982,801, filed 26 Oct. 2007, each of which is incorporated herein by reference in its entirety.

The present invention relates to a novel use of a malaria antigen to immunise against malarial disease. The invention relates in particular to the use of circumsporozoite (CS) protein from P. falciparum or fragments thereof, to immunise infants against malarial disease.

Malaria is one of the world's major health problems. During the 20th century, economic and social development, together with anti malarial campaigns, have resulted in the eradication of malaria from large areas of the world, reducing the affected area of the world surface from 50% to 27%. Nonetheless, given expected population growth it is projected that by 2010 half of the world's population, nearly 3.5 billion people, will be living in areas where malaria is transmitted[1]. Current estimates suggest that there are well in excess of 1 million deaths due to malaria every year, and the economic costs for Africa alone are thought to be staggering and in the region of at least several billion US dollars annually[2].

These figures highlight the global malaria crisis and the challenges it poses to the international health community. The reasons for this crisis are multiple and range from the emergence of widespread resistance to available, affordable and previously highly effective drugs, to the breakdown and inadequacy of health systems to the lack of resources. Unless ways are found to control this disease, global efforts to improve health and child survival, reduce poverty, increase security and strengthen the most vulnerable societies will fail.

One of the most acute forms of the disease is caused by the protozoan parasite *Plasmodium falciparum* which is responsible for most of the mortality attributable to malaria.

The life cycle of *Plasmodium* is complex, requiring two hosts, man and mosquito for completion. The infection of man is initiated by the introduction of sporozoites from the saliva of a biting and infected mosquito. The sporozoites migrate to the liver and there infect hepatocytes where they differentiate and multiply, via the exoerythrocytic intracellular stage, into the merozoite stage which infects red blood cells (RBC) to initiate cyclical replication in the asexual blood stage. The cycle is completed by the differentiation of a number of merozoites in the RBC into sexual stage gametocytes, which are ingested by the mosquito, where they develop through a series of stages in the midgut to produce sporozoites which migrate to the salivary gland.

The sporozoite stage of *Plasmodium* has been identified as a potential target of a malaria vaccine. Vaccination with inactivated (irradiated) sporozoite has been shown to induced protection against experimental human malaria (Am. J, Trop. Med. Hyg 24: 297-402, 1975). However, it is has not been possible practically and logistically to manufacture a vaccine for malaria for the general population based on this methodology, employing irradiated sporozoites.

The major surface protein of the sporozoite is known as circumsporozoite protein (CS protein). It is thought to be involved in the motility and invasion of the sporozoite during its passage from the initial site of inoculation by the mosquito into the circulation, where it migrates to the liver.

The CS protein of *Plasmodia* species is characterized by a central repetitive domain (repeat region) flanked by non-repetitive amino (N-terminus) and carboxy (C-terminus) fragments. The CS protein in *P. falciparum* has a central repeat region that is highly conserved.

Several groups have proposed subunit vaccines based on various forms or parts of the circumsporozoite protein. Two of these vaccines based exclusively on the central repeat sequence have undergone clinical testing in the early 1980's; one is a synthetic peptide, the other is a recombinant protein (Ballou et al Lancet: Jun. 6 (1987) page 1277 onwards, and Herrington et al Nature 328:257 (1987)). These vaccines were successful in stimulating an anti-sporozoite response. Nonetheless, the magnitude of the response was disappointing, with some vaccinees not making a response at all. Furthermore, the absence of "boosting" of antibody levels after subsequent injections and results of in vitro lymphocyte proliferation assays suggested that T-cells of most of these volunteers did not recognise the immuno-dominant repeat. Furthermore the efficacy of these two vaccines was marginal with only one vaccinated volunteer failing to develop parasitemia. These vaccines therefore were not pursued any further.

WO 93/10152 and WO 98/05355 describe a vaccine derived from the CS protein of *P. falciparum* and it clear that there has been some progress made towards the vaccination against *P. falciparum* using the approach described therein, see also Heppner et al. 2005, Vaccine 23, 2243-50.

The CS protein from *P. falciparum* has been cloned, expressed and sequenced for a variety of strains for example the NF54 strain, clone 3D7 (Caspers et al., Mol. Biochem. Parasitol. 35, 185-190, 1989). The protein from strain 3D7 is characterised by having a central immunodominant repeat region comprising a tetrapeptide Asn-Ala-Asn-Pro repeated 40 times but interspersed with four minor repeats Asn-Val-Asp-Pro. In other strains the number of major and minor repeats varies as well as their relative position. This central portion is flanked by an N and C terminal portion composed of non-repetitive amino acid sequences designated as the repeatless portion of the CS protein.

GlaxoSmithKline Biologicals' RTS,S malaria vaccine based on CS protein has been under development since 1987 and is currently the most advanced malaria vaccine candidate being studied[4]. This vaccine specifically targets the pre-erythrocytic stage of *P. falciparum*, and confers protection against infection by *P. falciparum* sporozoites delivered via laboratory-reared infected mosquitoes in malaria-naïve adult volunteers, and against natural exposure in semi-immune adults[5,6].

RTS,S/AS02A (RTS,S plus adjuvant system) was used in consecutive Phase I studies undertaken in The Gambia involving children aged 6-11 and 1-5 years, which confirmed that the vaccine was safe, well-tolerated and immunogenic[7]. Subsequently a pediatric vaccine dose was selected and studied in a phase I study involving Mozambican children aged 1-4 years where it was found to be safe, well tolerated and immunogenic[8].

WO 2006/029887 describes use of RTS,S to treat severe malaria in children 1 to 4 years of age.

Severe malaria disease is described in the WHO guide to clinical practice (Page: 4 World Health Organization. Management of severe malaria, a practical handbook. Second edition, 2000. http://mosquito.who.int/docs/hbsm.pdf). Classification of children according to the WHO-based definition for severe malaria identifies children who are very sick and at high risk of dying. High risk may be taken to mean about a 30% or greater risk dying.

In the 026 clinical study children aged 1-4 in Mozambique the overall efficacy of the vaccine against infection was calculated to be in the range 45% as measured as a delay in the time to on set of detection of parasites in the blood of a relevant child. The percentage protection against clinical disease was in the range of 35% and the percentage protection against severe malaria disease was in the range of 50%. This level of efficacy was found to persist for a period of about 18 months. (Alonso et al Lancet: 204, 364, page 1411-1420 205, and Lancet 366 pages 2012-2018.)

In the 026 trial there was no evidence of an interaction between age and general vaccine efficacy against non-severe clinical malaria disease, suggesting that efficacy did not significantly change with increasing age. However further exploratory subgroup analysis was carried out to estimate vaccine efficacy in the younger age groups that carry the brunt of malaria disease.

Interestingly this sub-analysis seemed to suggest that efficacy against severe malaria may have been higher in younger children in that trial. There was no suggestion from this analysis that the protection against infection or general efficacy i.e. retarding the development of clinical malaria symptom generally was better in the younger age group.

As far as the inventors are aware only one malaria vaccine has been given to infants under the age of 1 for a number of reasons, including potential toxicity concerns of experimental formulations containing novel adjuvants and/or theories that the immune system of infants is immature and thus no effective protection against malarial infection would be elicited by said vaccination. The strong adjuvants employed in malaria formulations, for example comprising QS21 and/or MPL are not generally used in pediatric vaccines. Instead vaccines for infants generally employ the older aluminium salt adjuvants.

However, a trial in Gambian employing a malaria vaccine SPf66 was performed in infants aged 6 to 11 months (Alonso et al Parasite Immunology, 1997: 19: 579-581). In areas of intense transmission in Tanzania SPf66 had shown 31% protection against first attack of malaria in children aged 1 to 4 years. Nevertheless when tested in infants aged 6 to 11 months the results seemed to indicate that the incidence of clinical malaria in children that had received the SPf66 vaccine were higher than those infants who received the control formulation, which was an inactivated polio vaccine. The effect was most marked in infants who had received a high dose of SPf66.

A recent clinical trial (referred to herein as 038 study) was performed in infants some as young as 10 weeks old at first vaccine administration, with some surprising results (see discussion below).

The present invention provides the use of an antigen derived from the CS protein of *Plasmodium falciparum* in combination with a pharmaceutically acceptable adjuvant, in the manufacture of a medicament for vaccinating infants against malaria.

BRIEF DESCRIPTION OF THE FIGURES

FIG. 1 shows an outline of the study design for trial 038
FIG. 1a shows an outline of the trial design
FIG. 2c shows proportion of doses with solicited general symptoms reported during the 7 days post vaccination
FIG. 3 shows vaccine efficacy data.
FIG. 4 shows a Kaplan-Meier curve for 038 trial
FIG. 5a shows a Kaplan-Meier curve for 026 trial (comparison data)
FIG. 5b shows a Kaplan-Meier curve for 026 trial (comparison data)

In FIG. 3 the table presents estimates of VE over a follow-up from 14 days post dose 3 of RTSS or Engerix until month 6 (cross-sectional visit) for the ATP cohort. This includes subjects that received at least 3 doses of RTS,S or Engerix-B, clearance drug and have follow-up time in ADI. Both estimates of VE against infection and disease are presented. Protocol Exploratory endpoint evaluating disease over a time-frame from month 0 (day of first vaccination) to month 6 for the ITT cohort is presented Disease 3.

In FIG. 3:
PYAR: Episodes/Person Years at Risk;
VE: Vaccine Efficacy;
CI: Confidence Interval

Figure 2A:
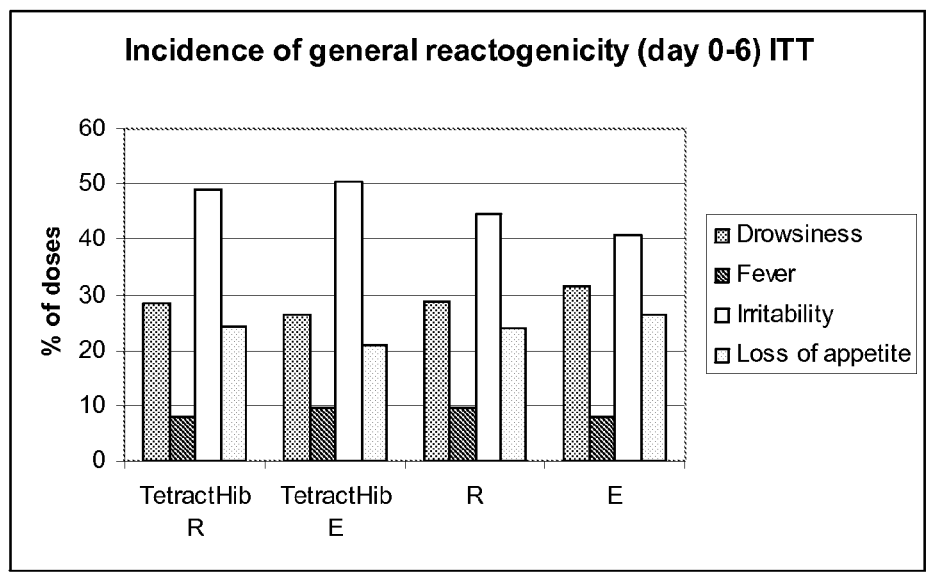
FIG. 2a shows incidence of general reactogenicity
Figure 2B:
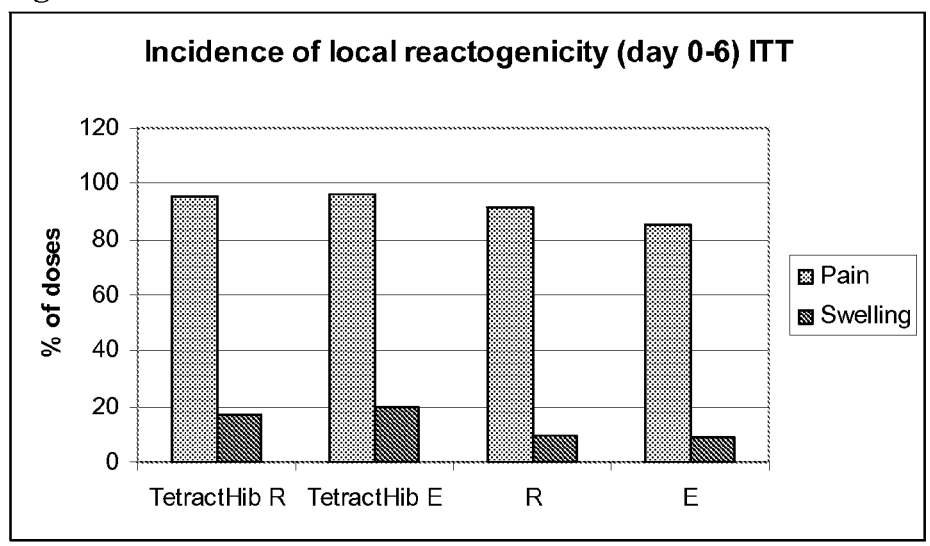
FIG. 2b shows incidence of local reactogenicity

[a] time to first episode; the presence of *P. falciparum* asexual parasitemia >0 per μL

[b] time to first episode; the presence of *P. falciparum* asexual parasitemia >500 per μL and the presence of fever ≥37.5° C. in a child who is unwell and brought for treatment

[c] time to first episode; any level of *P. falciparum* asexual parasitemia and the presence of fever ≥37.5° C. or a history of fever within 24 hours in a child who is unwell and brought for treatment

[d] time to first episode; the presence of *P. falciparum* asexual parasitemia >500 per μL and the presence of fever ≥37.5° C. in a child who is unwell and brought for treatment (ITT 0-6)

Adjusted estimates for area and distance from health center

Malaria in the context of this specification is intended to refer to malaria infection (defined below) and/or clinical malaria disease (also defined below).

In one embodiment the vaccination according to the invention provides a reduced risk of malaria infection. In one aspect the calculated reduction in risk of infection after vaccination is at least about 30, 40, 50%, for example 60 such as 65%.

In one embodiment the vaccination according to the invention provides a reduced risk of developing clinical symptoms of malaria. In one aspect the risk of clinical disease after receiving, for example three doses in a 3 month study interval may be reduced by at least about 30, 40, 50%, for example 60 such as approximately 65% following the third dose.

In one embodiment the malaria is non-severe malaria.

In one embodiment the vaccination provides a reduced risk of developing the following clinical disease symptoms: any level of *P. falciparum* asexual parasitemia and the presence of fever ≥37.5° C. or a history of fever within 24 hours.

In one aspect the reduced risk of malaria infection and/or reduced risk of developing clinical symptoms of malaria is assessed over the 3 months after final vaccination.

In the 038 study 3 doses of RTS,S with adjuvant in a pediatric formulation were given to infants at three time points at approximately monthly intervals (or 4 weekly intervals) nominally time points 0, 1 month and then 2 months. The latter regime forms one aspect of the invention.

The vaccine may be administered at appropriate intervals, for example 2, 3, 4 or 5 week intervals such as 4 week intervals as one, two or three doses.

Many of these infants were very likely truly naïve to malarial infection because of virtually no exposure to infected mosquitoes.

No significant safety or toxicity issues were raised and in fact the malarial vaccines in the study showed similar reactogenicity profiles to a commonly used infant vaccine TETRActHib™ from Aventis Pasteur, which contains antigens to at least diphtheria, tetanus, pertussis and also similar reactogenicity to a Hepatitis B vaccine Engerix-B™.

Furthermore and surprisingly the calculated efficacy of the malaria vaccine employed in the 038 study was about 65% (adjusted vaccine efficacy) against clinical malaria (that is general/non-severe) in comparison to the control group (data in Table 3). This efficacy is about 30% higher than the efficacy, observed in older children, against clinical non-severe disease results of the 026 trial, where the efficacy against non-severe malaria was between 30 and 35%. The latter figures reflect efficacy against non-severe clinical malaria symptoms and not efficacy against severe malaria, which was performed as a sub-analysis in the 026 trial. Thus the vaccination of the present invention seems to translate into a reduction of the risk of acquiring non-severe clinical form of malaria in comparison to the control group in this study and furthermore in comparison vaccinated older children in the 026 trial.

Clinical malaria is defined herein as fever greater than or equal to 37.5° C. with an asexual parasitaemia of *P. falciparum* of 500 present per μL of blood or more (for example with a sensitivity and specificity of greater than 90%).

Also surprising was the fact that the percentage protection against infection seen in the 038 trial was about 65% (Table 3), which the inventors believe is unprecedented and unexpected as the comparable result in the 026 trial was about 45%.

The efficacy data in the two trials (038, see Table 3, and 026) was derived from observations periods that differed in length.

Malaria infection in this context is intended to refer to any asexual *Plasmodium falciparum* parasitaemia detected by active detection of infection (ADI) or passive case detection (PCD).

At the three month monitor time point (that is 3 months after last vaccination) less than 20% about 17% of the infants vaccinated with the malaria vaccine in the 038 trial showed any signs of infection in comparison to more than 40% in the group that had received the comparator/control vaccination.

These observations lead the inventors to the conclusion that in fact the optimal age group for vaccination to provide protection against infection with malarial parasites and clinical malaria is infants.

Infant in the context of this specification is under 1 year such as about 1, 2, 3, 4, 5, 6, 7, 8, 9, 10, 11, 12, 13, 14, 15, 16, 17, 18, 19, 20, 25, 30, 35, 40, 45, 50 weeks old. More specifically, about 10, about 14 and/or about 18 weeks old.

In one embodiment a first vaccination is given to an infant at approximately 6 to 10 weeks after birth, such as 10 weeks.

In one embodiment a second vaccination is given to an infant at approximately 10 to 14 weeks after birth, such as 14 weeks.

In one embodiment a third vaccination is given to an infant at approximately 14 to 18 weeks after birth, such as 16-18 weeks.

A boosting vaccination may be provided after the first course vaccination has been administered. This boost may be administered 6 to 24 months after completion of said primary course.

Whilst not wishing to be bound by theory, the evidence available in this 038 trial does not suggest the anti CS titers were significantly different to those observed in the 026 trial, even though a trend toward higher GMT is seen in 038 for data up to 3 months post dose 3.

Thus it may be advantageous to provide the malaria vaccine to naïve infants before significant natural exposure to malarial infection.

Naïve in the context of this specification is intended to mean that the infant has no or very low detectable antibodies to the CS protein, for example as determined by ELISA or that the infant is so young that it is reasonable to believe that it has not experienced infection by *P. falciparum* parasites post natal.

A low level is below the cut off level defined for a relevant anti CS ELISA. See for example Gorden et al J. Infectious Disease 1995; 171:1576-1585 or Stout el al J. Infectious Diseases 1998; 178: 1139-1144 for further information in relation to suitable assays.

In one aspect of the invention at least 65% of the infants treated with the vaccine are naïve, such as 75, 85, 90, 95 or 99%.

After birth it may be advantageous to protect an infant from exposure to malarial infection by spraying homes and living quarters/bedrooms and the like with insecticide such as DDT. Alternative or additional protection can also be provided by bed nets, which may also be treated with suitable insecticide. These steps may assist in keeping the infant naïve until the malaria vaccine can be administered.

Interestingly in the 038 trial there seemed to be a suggestion that there was a correlation between the level of antibodies generated and protection provided by said vaccination. Infants with CS antibody levels in the highest tertile had 71% lower hazard risk of infection than those in the lower tertile.

In one aspect the invention provides a use of the vaccination for generating an appropriate antibody response to a CS protein, for example wherein 80, 85, 90, 95, 96, 97 or 98% of infants vaccinated according to the invention have anti-CS antibodies above the defined cut off limit for relevant ELISA (such as that used by GSK in clinical trials), about one month to about 4 months after receiving the last vaccination, such as one month and 4 months thereafter.

In one embodiment the antibody response is sufficient to provide a reduced risk of malarial infection and/or a reduced risk of clinical malaria in the vaccinated infant.

In an aspect the invention provides use of a vaccine for delaying infections of an infant with malaria parasites and/or delaying the development of clinical symptoms of malaria. The time to the first malaria infection episode or clinical malaria can, for example be measured using a Cox regression model.

The invention is particularly concerned with reducing the incidence of clinical malaria from *P. falciparum*, such as severe and/or mild forms thereof. Nevertheless in one aspect the invention provided protection against clinical symptoms of non-severe malaria.

Non-severe malaria is herein defined as all clinical cases of malaria that are not severe.

The CS antigens according to the invention may be used in conjunction with another antigen selected from any antigen which is expressed on the sporozoite or the pre-erythrocytic stage of the parasite life cycle such as the liver stage, for example liver stage antigen-1 (LSA-1), liver stage antigen-3 (LSA-3), thrombospondin related anonymous protein (TRAP), merozoite surface protein-1 (MSP1) the major merozoite surface protein, and apical merozoite antigen-1 (AMA-1) which has recently been show to be present at the liver stage (in addition to the erythrocytic stage). All of these antigens are well known in the field. The antigen may be the entire protein or an immunogenic fragment thereof. Immunogenic fragments of malaria antigens are well know, for example the ectodomain from AMA-1.

In one embodiment the *P. falciparum* antigen is fused to the surface antigen from hepatitis B (HBsAg). Thus a circumsporozoite (CS) protein antigen suitable for use in the present invention is in the form of a fusion protein with HBsAg. The antigen may be the entire CS protein from *P. falciparum* or part thereof, including a fragment or fragments of the CS protein, which may be fused together.

In one embodiment the CS protein based antigen is in the form of a hybrid protein comprising substantially all the C-terminal portion of the CS protein of *P. falciparum*, four or more tandem repeats of the CS protein immunodominant region, and the surface antigen from hepatitis B (HBsAg). In one aspect the fusion protein comprises a sequence which contains at least 160 amino acids which is substantially homologous to the C-terminal portion of the CS protein.

In particular "substantially all" the C terminal portion of the CS protein includes the C terminus devoid of the hydrophobic anchor sequence. The CS protein may be devoid of the last 12 to 14 (such as 12) amino-acids from the C terminal.

In one embodiment the fusion protein for use in the invention is a protein which comprises a portion of the CS protein of *P. falciparum* substantially as corresponding to amino acids 207-395 of *P. falciparum* 3D7 clone, derived from the strain NF54 (Caspers et al, supra) fused in frame via a linear linker to the N-terminal of HBsAg. The linker may comprise part or all of the preS2 region from HBsAg.

A suitable CS constructs for use in the present invention are as outlined in WO 93/10152. Particularly suitable is the hybrid protein known as RTS as described in WO 93/10152 (wherein it is denoted RTS*) and WO 98/05355, the whole contents of both of which are incorporated herein by reference.

A particularly suitable fusion protein is the fusion protein known as RTS which consists of:

A methionine-residue, encoded by nucleotides 1059 to 1061, derived from the *Sacchromyes cerevisiae* TDH3 gene sequence. (Musti A. m. et al Gene 1983 25 133-143).

Three amino acids, Met Ala Pro, derived from a nucleotide sequence (1062 to 1070) created by the cloning procedure used to construct the hybrid gene.

A stretch of 189 amino acids, encoded by nucleotides 1071 to 1637 representing amino acids 207 to 395 of the circumsporozoite protein (CSP) of *Plasmodium falciparum* strain 3D7 (Caspers et al, supra).

An amino acid (Gly) encoded by nucleotides 1638 to 1640, created by the cloning procedure used to construct the hybrid gene.

Four amino acids, Pro Val Thr Asn, encoded by nucleotides 1641 to 1652, and representing the four carboxy terminal residues of the hepatitis B virus (adw serotype) preS2 protein (Nature 280: 815-819, 1979).

A stretch of 226 amino acids, encoded by nucleotides 1653 to 2330, and specifying the S protein of hepatitis B virus (adw serotype).

In one embodiment the RTS is in the form of immunogenic particles of RTS,S.

The RTS,S construct may for example comprises two polypeptides RTS and S that are synthesized simultaneously and spontaneously form composite particulate structures (RTS,S).

The RTS protein is preferably expressed in genetically engineered yeast cells, most preferably *S. cerevisiae* or *Picha pastoris*. In such a host, RTS will be expressed as lipoprotein particle (also referred to herein as immunogenic particle or a virus like particle). The preferred recipient yeast strain preferably already carries in its genome several integrated copies of a hepatitis B S expression cassette. The resulting strain synthesizes therefore two polypeptides, S and RTS, that spontaneously co-assemble into mixed (RTS,S) lipoprotein particles. These particles, advantageously present the CSP sequences of the hybrid at their surface. Advantageously the ratio of RTS:S in these mixed particles is, for example 1:4.

It is believed that the presence of the surface antigen from Hepatitis B and the formation of the RTS,S particles boosts the immunogenicity of the CS protein portion of the hybrid protein, aids stability, and/or assists reproducible manufacturing of the protein.

Alternatively the hybrid protein may contain an N-terminal fragment from the CS protein of *P. falciparum*.

In one aspect the hybrid protein may comprise one or more repeat units from the central region of *P. falciparum*. For example 1, 2, 3, 4, 5, 6, 7, 8, 9 or more repeat units.

Alternatively the hybrid protein may contain a C-terminal fragment from the CS protein of *P. falciparum*.

Whilst not wishing to be bound by theory it is thought that the N and C terminus and the central repeat fragments may include several T and B cell epitopes.

In recombinant proteins often unnatural amino acids are introduced in the cloning process and are observed in the final expressed protein. For example several such as 1, 2, 3, 4 or 5 amino acids may be inserted at the beginning (N-terminus) of the protein. If 4 amino acids are inserted at the beginning of the protein they may for example be MMAP. In addition to or alternatively 1, 2, or 3 such as 1 amino acids may be inserted into the body/middle of the protein, provided that the activity and properties, such as immunogenicity, of the protein are not adversely affected.

The use of the malaria vaccine described here may also be in combination with one or more other vaccines commonly administered to infants less than 1 year of age, for example to provide protection against one or more the following: diphtheria, tetanus, pertusis, measles, oral polio and/or Hepatitis B. For example such vaccines may be given at age 1, 2, 3, 4, 5, 6, 7, 8, or 9 months as appropriate such as 6, 10 and 14 weeks. In one aspect said infant vaccine provided is DTPw-Hib optionally with an oral polo vaccine.

The malaria vaccine according to the invention may also be used in combination with a BCG vaccine, for example given 1, 2 or more weeks before the vaccine of the invention.

Vaccines such as oral polio, BCG and/or Hepatitis B vaccine may be given at about 1 week or less post natal.

When the malaria vaccine of the invention is given in conjunction with another one or more infant vaccine then the vaccines may be given simultaneously or about 15, 20, 25 or more days apart. The latter may avoid any adverse interaction of the two or more vaccines.

The invention also relates to a method of treatment comprising administering a therapeutically effective amount of a vaccine as described herein, to infants to provide protection against infection and/or developing clinical malaria.

A suitable vaccination schedule for use in the invention includes the administration of 3 doses of vaccine, at one month intervals. In the alternative embodiments of the invention one, two, three or more doses are employed, given 1, 2, 3, 4, 5, 6, 7, 8 or more weeks apart. Boosting of the same may be employed to complement the above primary course of vaccination.

It may also be appropriate to use general good practice for the prevention of malaria in conjunction with the malaria vaccine described herein. Best practice would include practices such spraying bedrooms etc with insecticides and/or employing a bed net to reduce the exposure of the individual to the mosquitoes. In the 038 trial such practices were used in conjunction with the RTS,S based malaria vaccine.

As the primary endpoint in the 038 trial, clinical episodes of malaria may for example be required to have the presence of *P. falciparum* asexual parasitemia above 500 or above 0 per μL on Giemsa stained thick blood films and the presence of fever (temperature ≥37.5° C.).

The definition for severe malaria may, for example include the presence of one or more of the following: severe malaria anaemia (PCV <15%), cerebral malaria (Blantyre coma score <2) or severe disease of other body systems which could include multiple seizures (two or more generalized convulsions in the previous 24 hours), prostration (defined as inability to sit unaided), hypoglycaemia <2.2 mmol/dL or <40 mg/dL), clinically suspected acidosis or circulatory collapse. These are given in Table 1 below.

| Severe malaria anemia | Asexual parasitemia definitive reading Hematocrit <15% No other more probable cause of illness | |
|---|---|---|
| Cerebral malaria | Asexual parasitemia definitive reading Coma score ≤2 No other identifiable cause of loss of consciousness | Assess coma score after correction of hypoglycemia and 60 minutes after control of fits. If fitting cannot be controlled within 30 minutes child is included |
| Severe malaria (other) | Asexual parasitemia definitive reading No other more probable cause of illness Does not meet criteria for severe malaria anemia or cerebral malaria One of the following: | |
| | Multiple seizures | Two or more generalized convulsions within a 24-hour period prior to admission |
| | Prostration | Inability to sit unaided |
| | Hypoglycemia | <2.2 mmol/dL or <40 mg/dL |
| | Acidosis | Document supportive signs and/or laboratory readouts |
| | Circulatory collapse | Document supportive signs and/or laboratory readouts |

In accordance with the invention, an aqueous solution of the purified hybrid protein may be used directly and combined with a suitable adjuvant or carrier. Alternatively, the protein can be lyophilized prior to mixing with a suitable adjuvant or carrier.

A suitable vaccine dose in accordance with the invention is between 1-100 μg antigen e.g. RTS,S per dose, such as 5 to 75 μg of antigen eg RTS,S, particularly a dose of 25 μg of antigen eg RTS,S protein, for example in 250 to 500 μl (final liquid formulation).

A particularly suitable dose of antigen for pediatric formulations according to the invention is 25 μg, for example in a final volume of 0.5 ml.

In one aspect in accordance with the invention the antigen is combined with an adjuvant or carrier.

Particularly an adjuvant is present, such as an adjuvant which is a preferential stimulator of a Th1 type response.

Suitable adjuvants include but not limited to, detoxified lipid A from any source and non-toxic derivatives of lipid A, saponins and other immunostimulants which are preferential stimulators of a Th1 cell response (also herein called a Th1 type response).

An immune response may be broadly divided into two extreme categories, being a humoral or cell mediated immune response (traditionally characterised by B lymphocytes producing antigen specific antibodies and T lymphocytes acting as antigen specific cellular effectors of protection. TH1 type responses (favouring the cell mediated effector immune responses) and TH2 type response (favouring the induction of antibody response).

Extreme TH1-type immune responses may be characterised by the generation of antigen specific, haplotype restricted cytotoxic T lymphocytes, and natural killer cell responses. In mice TH1-type responses are often characterised by the generation of antibodies of the IgG2a subtype, whilst in the human these correspond to IgG1 type antibodies. TH2-type immune responses are characterised by the generation of a range of immunoglobulin isotypes including in mice IgG1.

It can be considered that the driving force behind the development of these two types of immune responses are cytokines. High levels of TH1-type cytokines tend to favour the induction of cell mediated immune responses to the given antigen, whilst high levels of TH2-type cytokines tend to favour the induction of humoral immune responses to the antigen.

The distinction of TH1 and TH2-type immune responses is not absolute, and can take the form of a continuum between these two extremes. In reality an individual will support an immune response which is described as being predominantly TH1 or predominantly TH2. However, it is often convenient to consider the families of cytokines in terms of that described in murine CD4 positive T cell clones by Mosmann and Coffman (Mosmann, T. R. and Coffman, R. L. (1989) *TH1 and TH2 cells: different patterns of lymphokine secretion lead to different functional properties. Annual Review of Immunology*, 7, p 145-173). Traditionally, TH1-type responses are associated with the production of the INF-γ cytokines by T-lymphocytes. Other cytokines often directly associated with the induction of TH1-type immune responses are not produced by T-cells, such as IL-12. In contrast, TH2-type responses are associated with the secretion of IL-4, IL-5, IL-6, IL-10 and tumour necrosis factor-β (TNF-β).

It is known that certain vaccine adjuvants are particularly suited to the stimulation of either TH1 or TH2-type cytokine responses. Traditionally indicators of the TH1:TH2 balance of the immune response after a vaccination or infection includes direct measurement of the production of TH1 or TH2 cytokines by T lymphocytes in vitro after restimulation with antigen, and/or the measurement (at least in mice) of the IgG1:IgG2a ratio of antigen specific antibody responses.

Thus, a TH1-type adjuvant is one which stimulates isolated T-cell populations to produce high levels of TH1-type cytokines when re-stimulated with antigen in vitro, and induces antigen specific immunoglobulin responses associated with TH1-type isotype.

Adjuvants which are capable of preferential stimulation of the TH1 cell response are described in WO 94/00153 and WO 95/17209.

Preferred Th1-type immunostimulants which may be formulated to produce adjuvants suitable for use in the present invention include and are not restricted to the following.

It has long been known that enterobacterial lipopolysaccharide (LPS) is a potent stimulator of the immune system, although its use in adjuvants has been curtailed by its toxic effects. A non-toxic derivative of LPS, monophosphoryl lipid A (MPL), produced by removal of the core carbohydrate group and the phosphate from the reducing-end glucosamine, has been described by Ribi et al (1986, Immunology and Immunopharmacology of bacterial endotoxins, Plenum Publ. Corp., NY, p 407-419) and has the following structure:

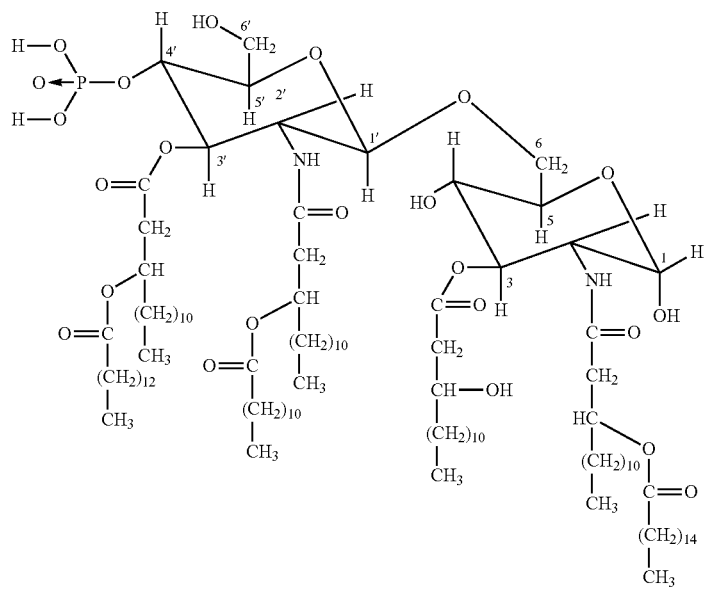

A further detoxified version of MPL results from the removal of the acyl chain from the 3-position of the disaccharide backbone, and is called 3-O-Deacylated monophosphoryl lipid A (3D-MPL). It can be purified and prepared by the methods taught in GB 2122204B, which reference also discloses the preparation of diphosphoryl lipid A, and 3-O-deacylated variants thereof.

A preferred form of 3D-MPL is in the form of an emulsion having a small particle size less than 0.2 µm in diameter, and its method of manufacture is disclosed in WO 94/21292. Aqueous formulations comprising monophosphoryl lipid A and a surfactant have been described in WO 98/43670.

The bacterial lipopolysaccharide derived adjuvants to be used in the present invention may be purified and processed from bacterial sources, or alternatively they may be synthetic. For example, purified monophosphoryl lipid A is described in Ribi et al 1986 (supra), and 3-O-Deacylated monophosphoryl or diphosphoryl lipid A derived from *Salmonella* sp. is described in GB 2220211 and U.S. Pat. No. 4,912,094. Other purified and synthetic lipopolysaccharides have been described (Hilgers et al., 1986, *Int. Arch. Allergy. Immunol.*, 79(4):392-6; Hilgers et al., 1987, Immunology, 60(1):141-6; and EP 0 549 074 B1). A particularly preferred bacterial lipopolysaccharide adjuvant is 3D-MPL.

Accordingly, the LPS derivatives that may be used in the present invention are those immunostimulants that are similar in structure to that of LPS or MPL or 3D-MPL. In another alternative the LPS derivatives may be an acylated monosaccharide, which is a sub-portion to the above structure of MPL.

Saponins are also suitable Th1 immunostimulants in accordance with the invention. Saponins are well known adjuvants and are taught in: Lacaille-Dubois, M and Wagner H. (1996. A review of the biological and pharmacological activities of saponins. Phytomedicine vol 2 pp 363-386). For example, Quil A (derived from the bark of the South American tree Quillaja Saponaria Molina), and fractions thereof, are described in U.S. Pat. No. 5,057,540 and "Saponins as vaccine adjuvants", Kensil, C. R., *Crit Rev Ther Drug Carrier Syst*, 1996, 12 (1-2):1-55; and EP 0 362 279 B1. The haemolytic saponins QS21 and QS17 (HPLC purified fractions of Quil A) have been described as potent systemic adjuvants, and the method of their production is disclosed in U.S. Pat. No. 5,057,540 and EP 0 362 279 B1. Also described in these references is the use of QS7 (a non-haemolytic fraction of Quil-A) which acts as a potent adjuvant for systemic vaccines. Use of QS21 is further described in Kensil et al. (1991. J. Immunology vol 146, 431-437). Combinations of QS21 and polysorbate or cyclodextrin are also known (WO 99/10008). Particulate adjuvant systems comprising fractions of QuilA, such as QS21 and QS7 are described in WO 96/33739 and WO 96/11711.

Another immunostimulant is an immunostimulatory oligonucleotide containing unmethylated CpG dinucleotides ("CpG"). CpG is an abbreviation for cytosine-guanosine dinucleotide motifs present in DNA. CpG is known in the art as being an adjuvant when administered by both systemic and mucosal routes (WO 96/02555, EP 468520, Davis et al., *J. Immunol*, 1998, 160(2):870-876; McCluskie and Davis, *J. Immunol.*, 1998, 161(9):4463-6). Historically, it was observed that the DNA fraction of BCG could exert an anti-tumour effect. In further studies, synthetic oligonucleotides derived from BCG gene sequences were shown to be capable of inducing immunostimulatory effects (both in vitro and in vivo). The authors of these studies concluded that certain palindromic sequences, including a central CG motif, carried this activity. The central role of the CG motif in immunostimulation was later elucidated in a publication by Krieg, Nature 374, p 546 1995. Detailed analysis has shown that the CG motif has to be in a certain sequence context, and that such sequences are common in bacterial DNA but are rare in vertebrate DNA. The immunostimulatory sequence is often: Purine, Purine, C, G, pyrimidine, pyrimidine; wherein the CG motif is not methylated, but other unmethylated CpG sequences are known to be immunostimulatory and may be used in the present invention.

In certain combinations of the six nucleotides a palindromic sequence is present. Several of these motifs, either as repeats of one motif or a combination of different motifs, can be present in the same oligonucleotide. The presence of one or more of these immunostimulatory sequences containing oligonucleotides can activate various immune subsets, including natural killer cells (which produce interferon γ and have cytolytic activity) and macrophages (Wooldrige et al Vol 89 (no. 8), 1977). Other unmethylated CpG containing sequences not having this consensus sequence have also now been shown to be immunomodulatory.

CpG when formulated into vaccines, is generally administered in free solution together with free antigen (WO 96/02555; McCluskie and Davis, supra) or covalently conjugated to an antigen (WO 98/16247), or formulated with a carrier such as aluminium hydroxide ((Hepatitis surface antigen) Davis et al. supra; Brazolot-Millan et al., *Proc. Natl. Acad. Sci.*, USA, 1998, 95(26), 15553-8).

Such immunostimulants as described above may be formulated together with carriers, such as for example liposomes, oil in water emulsions, and/or metallic salts, including aluminium salts (such as aluminium hydroxide). For example, 3D-MPL may be formulated with aluminium hydroxide (EP 0 689 454) or oil in water emulsions (WO 95/17210); QS21 may be advantageously formulated with cholesterol containing liposomes (WO 96/33739), oil in water emulsions (WO 95/17210) or alum (WO 98/15287); CpG may be formulated with alum (Davis et al. supra; Brazolot-Millan supra) or with other cationic carriers.

Combinations of immunostimulants are also preferred, in particular a combination of a monophosphoryl lipid A and a saponin derivative (WO 94/00153; WO 95/17210; WO 96/33739; WO 98/56414; WO 99/12565; WO 99/11241), more particularly the combination of QS21 and 3D-MPL as disclosed in WO 94/00153. Alternatively, a combination of CpG plus a saponin such as QS21 also forms a potent adjuvant for use in the present invention.

Thus, suitable adjuvant systems include, for example, a combination of monophosphoryl lipid A, preferably 3D-MPL, together with an aluminium salt.

An enhanced system involves the combination of a monophosphoryl lipid A and a saponin derivative particularly the combination of QS21 and 3D-MPL as disclosed in WO 94/00153, or a less reactogenic composition where the QS21 is quenched in cholesterol containing liposomes (DQ) as disclosed in WO 96/33739.

A particularly potent adjuvant formulation involving QS21, 3D-MPL & tocopherol in an oil in water emulsion is described in WO 95/17210 and is another preferred formulation for use in the invention.

Another preferred formulation comprises a CpG oligonucleotide alone or together with QS21, 3D-MPL or together with an aluminium salt.

Accordingly in one embodiment of the present invention there is provided the use of detoxified lipid A or a non-toxic derivative of lipid A, more preferably monophosphoryl lipid A or derivative thereof such as 3D-MPL, in combination with a malaria antigen as described herein, for the manufacture of a vaccine for the prevention of malaria disease and/or infection in infants.

In one embodiment of the invention a saponin, such as QS21, is used in combination with a malaria antigen as described herein, for the manufacture of a vaccine for the prevention of malaria disease and/or infection in infants or a method of treating an infant employing the same.

In one embodiment the invention provides use of detoxified lipid A or a non-toxic derivative of lipid A, more preferably monophosphoryl lipid A or derivative thereof such as 3D-MPL, in combination with a saponin, such as QS21, and a malaria antigen as described herein, for the manufacture of a vaccine for the prevention of malaria disease and/or infection in infants. The invention also extends to an method of treating an infant employing these aspects.

In one embodiment the invention further employs an oil in water emulsion or liposomes. Suitable combinations of adjuvants for use in the present invention are:
1. 3D-MPL, QS21 and an oil in water emulsion.
2. 3D-MPL and QS21 in a liposomal formulation.
3. 3D-MPL, QS21 and CpG in a liposomal formulation.

The amount of 3D-MPL used is generally small, but depending on the vaccine formulation may be in the region of 1-1000 µg per dose, generally 1-500 µg per dose, such as between 1 to 100 µg per dose (10, 15, 20, 25, 30, 35, 40, 45, 50, 60, 70, 80 or 90 µg per dose).

The amount of saponin for use in the adjuvants of the present invention may be in the region of 1-1000 µg per dose, generally 1-500 µg per dose, more such as 1-250 µg per dose, and more specifically between 1 to 100 µg per dose (10, 15, 20, 25, 30, 35, 40, 45, 50, 60, 70, 80 or 90 µg per dose).

The amount of CpG or immunostimulatory oligonucleotides in the adjuvants or vaccines of the present invention is generally small, but depending on the vaccine formulation may be in the region of 1-1000 µg per dose, generally 1-500 µg per dose, and more such as between 1 to 100 µg per dose (10, 15, 20, 25, 30, 35, 40, 45, 50, 60, 70, 80 or 90 µg per dose).

In one aspect of the invention the dose has a final volume of 0.5 ml.

The vaccines of the invention may be provided by any of a variety of routes such as oral, topical, subcutaneous, mucosal), intravenous, intramuscular, intranasal, sublingual and intradermal.

Immunisation can be prophylactic or therapeutic. The invention described herein is primarily but not exclusively concerned with prophylactic vaccination against malaria, more particularly prophylactic vaccination to prevent or to reduce the likelihood of malarial infection and/or malaria disease.

Appropriate pharmaceutically acceptable carriers or excipients for use in the invention are well known in the art and include for example water or buffers. Vaccine preparation is generally described in Pharmaceutical Biotechnology, Vol. 61 Vaccine Design—the subunit and adjuvant approach, edited by Powell and Newman, Plenum Press New York, 1995. New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

In the context of this specification comprising is to be interpreted as including.

Aspects of the invention comprising a certain element are also intended to extend to said aspects consisting or consisting essentially of the relevant elements and vice versa, if appropriate

EXAMPLE

Study Design

The study was conducted at the Centro de Investigação em Saude de Manhiça (CISM, Manhiça Health Research Centre) between June 2005 and March 2007, in Ilha Josina and Taninga, two communities about 50 km north of the town of Manhiça, where CISM headquarters are located. Characteristics of the overall study area and of Ilha Josina have been previously described (Alonso P L, Sacarlal J, Aponte J J, Leach A, Macete E, Milman J, et al. Efficacy of the RTS,S/

AS02A vaccine against *Plasmodium falciparum* infection and disease in young African children: randomised controlled trial. Lancet 2004 Oct. 16-22; 364(9443):1411-20). Taninga is a rural community facing Ilha Jossina directly across the flood plain of the Incomati River. The climate is subtropical with two distinct seasons: a warm and rainy season from November to April and a generally cool and drier season during the rest of the year. Malaria transmission is perennial with some seasonality and mostly attributable to *P. falciparum*. *Anopheles funestus* is the main vector. Combination therapy based on amodiaquine and sulphadoxine-pirimethamine was the first line treatment for uncomplicated malaria until September 2006 when it was changed to artemisinin based combination therapy (ACT) using artesunate and sulphadoxine-pyrimethamine. Since 2005, yearly rounds of indoor residual spraying (IRS) have been carried out as part of the malaria control activities of the Ministry of Health. During the first round in December 2005, IRS was based on Carbamates (ICON®) but this was changed to DDT in December 2006. As part of the study activities and in accordance with national recommendations, an insecticide treated bed net (ITN) was given to pregnant women at screening, along with instructions for its use. Both Ilha Josina and Taninga have primary health posts and maternities that provide basic curative and preventive care. For the study, facilities were upgraded, around the clock care was available, and transport provided for referrals to the Manhica District Hospital, adjacent to CISM.

The study was a phase I/IIb double blind randomized controlled trial to assess the safety, immunogenicity and efficacy test of concept of the RTS,S/AS02D candidate malaria vaccine when administered to infants by immunisations given at 10, 14 and 18 weeks of age. The protocol was approved by the Mozambican National Bioethics Committee, the Hospital Clinic of Barcelona Ethics Review Committee and the PATH Human Subjects Protection Committee. Trial registration number is NCT00197028 and IND number is BB-IND 10514. The trial was undertaken according to the International Conference of Harmonization Good Clinical Practices guidelines and was monitored by GSK Biologicals. A Local Safety Monitor and a Data and Safety Monitoring Board closely reviewed the design conduct and results of the trial.

Participants

CISM operates a demographic surveillance system in about half of the district which includes both study locations. Pregnant women in their third trimester of pregnancy, resident in the study area, who would consider enrolling their infants, were asked to take part in the informed consent process. At first visit, an information sheet was read and explained to groups of pregnant women by specially trained staff. We sought individual consent only after the women passed an individual oral comprehension test designed to check understanding of the information. They were invited to sign (or thumbprint if not literate) the informed consent document. A member of the community, not associated with the research study, acted as an impartial witness and counter-signed the consent form. Those that gave informed consent received counselling and were screened for HIV (Determine™ HIV1-2, Abbot Laboratories and UNI-GOLD HIV, Trinity Biotech PLC) and Hepatitis B (Determine™ HBsAg, Abbot Laboratories). Women found to be HIV positive were referred to the government health services at the Manhiça District Hospital for medical evaluation and management following National Guidelines. These included reduction of mother to child transmission as well as the free provision of anti-retro viral therapy to those fulfilling clinical and social criteria. Hepatitis B positive mothers were counseled about the risk of transmission to the offspring and Hepatitis B vaccine at birth was offered to the newborn.

Following another informed consent of the mother, and using similar procedures as those previously described, infants were screened between 6 and 12 weeks of age. This included a brief medical history and physical examination and blood sampling by heel prick or venous puncture for baseline haematology, biochemistry and immunology. Inclusion criteria included, among others, a normal gestational period and absence of obvious medical abnormalities. Because children born to Hepatitis B and HIV-positive mothers are at a high risk of neonatal acquisition of the viruses, they were not included in the trial. Among other criteria, children were excluded from participation if BCG was not given at least one week before starting study vaccination or if any other vaccinations, other than the first dose of OPV given at birth with BCG, had been given prior to enrollment.

An individual photographic identification card was provided soon after recruitment. This included the name of the child and the mother as well as the personal identification number from the census (Alonso P, Saute F, Aponte J J. Manhiça DSS, Mozambique. In: Sankoh O A, Ngom P, Nyarko P, Mwageni E, Kahn K, editors. Population and health in developing countries; vol. 1, population, health and survival at INDEPTH sites. Ottawa: International development research center (IDRC); 2002. p. 189-95) and a unique study number issued at the screening visit. Field activities started on 24 Jun. 2005. The first infant was enrolled on 23 Aug. 2005 and the last one on 12 Sep. 2006. Follow-up activities for the double blind phase were completed on Mar. 6, 2007, when the last recruited child reached their 6 month study visit.

Procedures

EPI in Mozambique includes BCG vaccine and Oral Polio Vaccine (OPV) at birth, three doses of Dipheteria-Tetanus-Pertusis whole cell (DTPw) and Hepatitis B vaccines, co-administered with OPV at 8, 12 and 16 weeks of age and measles vaccine at 9 months of age. For the purpose of the study we introduced two changes to this scheme. Given that the use of Hib vaccine is fast expanding and is becoming part of EPI in a growing number of African countries, we decided to include it combined with DTPw as it would provide additional benefit for children participating in the trial. Hepatitis B vaccine was not given together with DTPw as RTS,S has been shown to induce comparable titers of anti-HBsAg. FIG. 1a represents the trial design and follow-up scheme. Eligible children were enrolled the day of the first vaccination with DTPw/Hib [TETRActHib™ Aventis Pasteur]. Children were randomly allocated, at the time of the first vaccination with DTPw/Hib, to receive three doses of either RTS,S/AS02D (GSK Biologicals, Rixensart. Belgium) or Hepatitis B vaccine (Engerix-B™, GSK Biologicals, Rixensart, Belgium) staggered by 2 weeks with DTPw/Hib and OPV vaccines and administered at 10, 14 and 18 weeks of age. Block randomization was done at GSK Biologicals with SAS software version 8 (1:1 ratio, block size of 2). The randomization code was released to the investigators once databases had been monitored, cleaned and locked.

The infants randomised to the paediatric formulation of the malaria vaccine group received 0.5 ml of the RTS,S/AS02D formulation containing 25 μg of RTS,S and the Adjuvant System AS02D. RTS,S is a hybrid recombinant protein consisting of the *P. falciparum* CS protein central tandem repeat and carboxy-terminal regions fused to the amino-terminus of the S antigen of hepatitis B virus (HBsAg). The proteins auto-assemble to form a particle that also includes unfused S antigen. Antigen and GlaxoSmithKline's proprietary AS02D Adjuvant System are described in detail elsewhere (Macete E V, Sacarlal J, Aponte J J, Leach A, Navia M M, Milman J, et al. Evaluation of two formulations of adjuvanted RTS, S malaria vaccine in children aged 3 to 5 years living in a malaria-endemic region of Mozambique: a Phase I/IIb randomized double-blind bridging trial. Trials 2007 Mar. 26; 8:11).

DTPw/Hib was administered by the intramuscular (IM) route in the right antero-lateral thigh while RTS,S/AS02D or Engerix-B™ were administered IM in the left antero-lateral thigh. The RTS,S/AS02D or Engerix-B™ vaccination was delivered in a double blind fashion (observer blinded, participant blinded). The vaccination team prepared the vaccine and masked the contents of the syringe with opaque tape before providing the syringe to the clinical team for immunisation of the infant. Since the two vaccines used in the study were of distinct appearance, the vaccination team was not blinded and was not involved in any other study procedure.

After each vaccination, infants were observed for at least one hour. Trained field workers visited the children at home every day for the following six days to record any adverse event (AE). Solicited local and general adverse events were recorded during this period. Unsolicited adverse events were recorded for 30 days after each dose through the health facility based morbidity surveillance system. Serious adverse events (SAEs) were detected in a similar way and recorded throughout the study. A detailed description of definitions for solicited and unsolicited adverse events as well as SAEs can be found elsewhere[11]. Further safety assessment was performed through haematological and biochemical assessments, including renal and hepatic function measured at several time points as shown in FIG. 1a. Anti-HBsAg antibody titres were measured at baseline and one month post dose 3 of RTS,S/AS02D or Engerix-B™. Anti-CS antibody titres were measured at baseline, and one and three and a half months post dose 3 of RTS,S/AS02D or Engerix-B™. Antibodies against diphtheria and tetanus toxins and polyribosyl ribitol phosphate (PRP) for *H. influenzae* type b were measured one month after dose 3 of DTPw/Hib. Antibodies against *B. pertussis*, were measured at baseline and one month after the 3rd dose of DTPw/Hib.

Cases of malaria infection by *P. falciparum* were monitored by active detection of infection (ADI) and by passive case detection (PCD) at health facilities in the study area. ADI consisted of repeated visits to study participants at predefined intervals (FIG. 1a). At each visit, a blood slide for parasitaemia determination was collected irrespective of the presence or absence of symptoms, and the axillary temperature was recorded. Children with positive slides were treated with first line treatment regardless of the presence of symptoms and excluded from further assessment of ADI. Before starting the ADI follow-up, asymptomatic parasitaemia was cleared presumptively in all children with a combination of amodiaquine (10 mg/kg/day for 3 days) and a single dose of sulfadoxine-pyrimethamine (sulfadoxine 25 mg/kg and pyrimethamine 1.25 mg/kg) administered two weeks prior to the third and final dose of RTS,S/AS02D or Engerix-B™ Parasitaemia was checked 2 weeks later at the time of the third dose and, if present, treated with second-line treatment based on Coartem®. Only children without parasitemia started the ADI, which commenced 2 weeks after the third dose of RTS,S/AS02D or Engerix-B™ and was performed every-other week for 12 weeks.

The health facility based morbidity surveillance system set up at the Manhiça District Hospital, Ilha Josina and Taninga health posts, enabled passive case detection (PCD) of all attendances to health facilities and ascertainment of episodes of clinical malaria. This surveillance system has been described in detail elsewhere (Alonso P L, Sacarlal J, Aponte J J, Leach A, Macete E, Milman J, et al. Efficacy of the RTS,S/AS02A vaccine against *Plasmodium falciparum* infection and disease in young African children: randomised controlled trial. Lancet 2004 Oct. 16-22; 364(9443):1411-20). In brief, the three facilities have 24 h medical staff trained to identify study participants through the personal identification card and to ensure standardized assessment, management and documentation throughout follow-up. All children with documented fever (37.5° C. or more) or history of fever in the preceding 24 h, or pallor had blood taken for parasite and packed cell volume (PCV) determinations. Children meeting admission criteria were referred to the Manhiça District Hospital for hospitalization. Clinical management was provided according to standard national guidelines. On admission and discharge all relevant information was recorded on standardised forms.

To determine parasite presence and density of *P. falciparum* asexual stages, Giemsa stained blood slides were read following standard quality-controlled procedures described elsewhere (Alonso P L, Sacarlal J, Aponte J J, Leach A, Macete E, Milman J, et al. Efficacy of the RTS,S/AS02A vaccine against *Plasmodium falciparum* infection and disease in young African children: randomised controlled trial. Lancet 2004 Oct. 16-22; 364(9443):1411-20). Biochemical parameters were measured using a dry biochemistry photometer VITROS DT II (Orto Clinical Diagnostics, Johnson & Johnson Company, USA). Haematological tests were performed using a Sysmex KX-21N cell counter (Sysmex Corporation Kobe, Japan). PCV was measured in heparinised microcapillary tubes using a Hawksley haematocrit reader after centrifugation.

Antibodies specific for the CS protein tandem repeat epitope were measured by a standard ELISA using plates absorbed with the recombinant antigen R32LR that contains the sequence [NVDP(NANP)15]2LR. The assay cut-off was set at 0.5 EU/ml. Anti-HBsAg antibody levels were measured using a commercial radioimmunoassay (AUSAB, Abbott) with an assay cut-off set at 10 IU/ml. Anti-PRP antibodies were measured by ELISA with a cut-off set at 0.15 μg/ml. Anti-diphtheria and anti-tetanus antibodies titres were measured by ELISA with an assay cut-off set at 0.10 IU/ml. Anti-whole-cell-B. Pertussis antibody titres were determined by ELISA (Labsystems) with an assay cut-off set at 15 EL.U/ml.

Statistical Analysis

The primary endpoints of the trial were safety and tolerability of the RTS,S/AS02D vaccine candidate. All children who received at least one dose of DTPw/Hib were included in the intention-to-treat (ITT) safety analysis.

Anti-CS and anti-HBsAg antibody data were summarised by Geometric Mean Titres (GMTs) with 95% CI. Anti-CS seropositivity was defined as ≥0.5 EU/ml, while seroprotection from Hepatitis B was defined as ≥10 IU/ml.

The test of concept for vaccine efficacy (VE) was based on a prospectively-defined Report & Analysis Plan (RAP) carried out on an According to Protocol (ATP) cohort. The ATP cohort included subjects that met all eligibility criteria, completed the vaccination course and contributed follow-up time during the ADI period. The analysis included all first or only asexual *P. falciparum* infections detected during the follow-up period starting 14 days after dose 3 of RTS,S/AS02D or Engerix-B™ and ending with the visit at study month 6 (approximately a 3 month follow-up). Malaria infections included in this analysis were detected by ADI or PCD.

Further exploratory analysis considered vaccine efficacy against clinical malaria in an ITT cohort that included first or only episodes from the time of enrollment until the date on which the last enrolled infant completed their ADI follow-up (Mar. 6, 2007). Additionally, exploratory analyses of clinical malaria were performed in the same ATP cohort and follow-up period as in the efficacy assessment of new infections. The primary case definition for clinical malaria was fever (axillary temperature ≥37.5° C.) with an asexual parasitaemia of *P. falciparum* of 500 or more per microliter. This definition has a reported sensitivity and specificity of greater than 90% (Saute F, Aponte J, Almeda J, Ascaso C, Abellana R, Vaz N, et al. Malaria in southern Mozambique: malariometric indicators and malaria case definition in Manhica district. Trans R Soc Trop Med Hyg 2003 November-December; 97(6):661-6). Other exploratory efficacy analyses used secondary case definitions for clinical malaria including fever or history of fever in the previous 24 hours plus any asexual *P. falciparum* parasitaemia. The time at risk, reported as person years at risk (PYAR), was adjusted for absences from the study area and for antimalarial drug usage as previously described (Alonso P L, Sacarlal J, Aponte J J, Leach A, Macete E, Milman J, et al. Efficacy of the RTS,S/AS02A vaccine against *Plasmodium falciparum* infection and disease in young African children: randomised controlled trial. Lancet 2004 Oct. 16-22; 364 (9443):1411-20), as these are periods of time when infants could not be expected to contribute study endpoints.

VE was defined as 1 minus the rate ratio. Vaccine efficacy was adjusted by distance to health facility, calculated according to previously described methods (Alonso P L, Sacarlal J, Aponte J J, Leach A, Macete E, Milman J, et al. Efficacy of the RTS,S/AS02A vaccine against *Plasmodium falciparum* infection and disease in young African children: randomised controlled trial. Lancet 2004 Oct. 16-22; 364(9443):1411-20) and community of residence. The adjusted vaccine efficacy, assessed using Cox regression models, is reported throughout the text unless otherwise stated. The effect of anti-CS antibody titres on the risk of malaria infection was evaluated in the group that received RTS,S/AS02D by comparing the hazard ratio (HR) of infants in the lowest response tertile against those in the highest response tertile, as well as estimating the HR per doubling of anti-CS antibody titre using Cox regression models. Finally, a comparison was made of the geometric mean titre of children who had at least one episode of malaria infection against those without documented malaria infection using a Wilcoxon Rank Sum test.

The sample size was based on the evaluation of vaccine safety. A trial with 100 subjects in each group had 80% power to detect a difference in the proportion of adverse events of 26% or more if the frequency of an event in the Engerix-B™ group was 10% or more. A trial of this size also had 90% power to detect an efficacy against malaria infection of 45% or more assuming an attack rate of 75% or more in the control group over the surveillance period. Analyses were performed using SAS and STATA.

Role of the Funding Source

GSK and CISM both received financial support to undertake the work described in this manuscript from the PATH Malaria Vaccine Initiative (MVI) that was involved in all aspects of the study design and interpretation (as per authorship guidelines). MVI funded this work through a grant from the Bill & Melinda Gates Foundation. Core funding for CISM is provided by the Spanish Agency for International Cooperation (AECI). Results Results FIG. 1 shows the trial profile. 326 out of 446 pregnant women fulfilled the eligibility criteria and delivered 329 newborns. Of those, 251 infants were screened and 214 (85%) of the screened children were enrolled in the trial and received the first dose of DTPw/Hib vaccine. 93 (86%) of the children in the RTS,S/AS02D and 92 (85%) in the Engerix-B™ group entered ADI follow-up. During the follow-up, consent was withdrawn from seven children in the RTS,S/AS02D group and eight children in the Engerix-B™ group. Three children in each group received the wrong vaccine at Dose 2 of RTS, S/AS02D or Engerix-B™. They were not included in the ATP analysis. Baseline characteristics for both groups are presented in Table 1.

FIG. 2c shows the proportion of all administered doses where a solicited symptom was recorded. The figure presents four groups, as the data for DTPw/Hib and OPV are segregated by randomisation assignment. The proportion of children with pain was high and similar in all groups. The relative proportion of symptoms was similar after each injection of RTS,S/AS02D and comparable in magnitude (data not shown). No grade 3 solicited symptom was documented in the RTS,S/AS02D group, and the incidence was very low in the other groups (data not shown). In the ITT cohort followed until end of follow-up on 6 Mar. 2007, there were 31 SAEs in the RTS,S/AS02D group and 30 SAEs in the Engerix-B™ group. None of them were reported as related to vaccination. There were four deaths during this same follow-up period; all of them after the ADI period had finished at study month 6 (2 in RTSS/AS02D group and 2 in the Engerix-B™ group). All of the deaths occurred at home. Verbal autopsies suggest that one death in the RTS,S/AS02D group was due to septic shock, and the remaining three due to gastroenteritis and severe dehydration. The values and proportion of abnormal haematology and biochemical values after Dose 1 and after Dose 3 were similar in both groups and do not raise any safety signal (data not shown).

For the 214 subjects enrolled in the trial (107 RTS,S/AS02D and 107 Engerix-B™) data for the EPI antigens responses are available for 151 subjects post dose 3 (76 in the RTS,S/AS02D and 75 in the control group). There are no differences in seroprotection/seropositivity and titers between the subjects in the two groups (Aide et al, manuscript in preparation). All but three children reached seroprotective levels against all EPI antigens. These three children will be re immunised with the antigens to which they have failed to respond.

Anti-CS and anti-HBsAg antibody levels measured against CS and HBsAg are shown in Table 2. At screening 24/76 (32%) and 26/77 (34%) of the infants in the RTS,S/AS02D and Engerix-B™ group, respectively, had low titres of detectable anti-CS antibodies. One month after dose 3, 99% (70/71) of infants that received RTS,S/AS02D had detectable anti-CS antibodies, while the corresponding figure among infants that received Engerix-B™ is 4% (3/68). Three and a half months after dose 3 (study month 6), the proportion of anti-CS positives in the RTS,S/AS02D remained high (98%) but the GMT had decreased. The anti-CS GMT in the Engerix-B™ group remained low, even though the prevalence of detectable antibodies increased to 20% (12/61). Response to hepatitis B was good in both groups (Table 2).

FIG. 4 shows the proportion of children with at least one episode of malaria infection during the ADI follow-up starting 14 days after dose 3 of RTS,S/AS02D or Engerix-B™ up to study month 6. A total of 68 new infection were documented during this follow-up period, 22 in the RTS,S/AS02D group and 46 in the Engerix-B™ group. The crude vaccine efficacy (VE) estimate was 62.2% (95% CI 37.1%; 77.3%, p=0.0002) over the 3 month follow-up period. Adjusted by distance to the health centre and community of residence, the VE was 65.9% (95% CI 42.6%; 79.8%, p <0.0001) (Table 3). The point prevalence of infection at study month 6 was similar between the two groups (5% in the RTS,S/AS02D group vs 8% in the control group, p=0.536), nor were there differences between mean parasite densities (2082 parasites per microliter (SD 5604) in the RTS,S/AS02D group vs 2579 (SD 6088) in the control group, p=0.85).

Exploratory endpoints contained in the RAP included efficacy estimates for clinical malaria using different cohorts and case definitions. Efficacy based on an ITT cohort followed from month 0 to month 6, using the primary case definition of malaria (first or only episode of fever with more than 500 parasites per microliter) detected through both ADI and PCD, was 35.5% (95% CI-7.5%; 61.3%, p=0.093). Further efficacy estimates for clinical malaria in an ATP cohort starting 14 days after dose 3 of RTS,S/AS02D or Engerix-B™ up to study visit at 6 months, the same follow-up period used in the primary VE estimate for infection, are shown in table 3. Table 4 gives details of further follow up for 12 months post dose 3, i.e. from 3-14 months.

The relation of anti-CS antibody titres to the risk of malaria was examined in a number of ways. Firstly, we compared anti-CS antibody titres after dose 3 of RTS,S/AS02D or Engerix-B™ in the group of infants where no malaria infection was documented during the follow-up versus those that had at least one episode. On average anti-CS antibody titres were higher in the former group (208 vs. 132, p=0.026).

Secondly, the hazard ratio was 71% lower among infants in the higher tertile of the distribution of antibodies than among infants in the lower tertile (95% CI 8.4%; 90.7%, p=0.035). Finally, we examined risk of malaria infection in relation to the increase in antibody titres. Doubling of antibody titres was associated with a reduction in the risk of a new infection of 6.4% (95% CI 10.8; 1.8) p=0.007. A ten times increase in anti-CS titers is associated with a 19.8% reduction in the risk of new infections (95% CI 31.6; 5.9).

Based on an analysis of the results vaccine efficacy for new infections was 65% over a 3 month follow-up period after completion of immunizations. This efficacy estimate is higher than the 45% reduction reported in a previous trial (026 trial) among older children aged 1 to 4 years followed in a comparable ADI system in the same study area (Alonso P L, Sacarlal J, Aponte J J, Leach A, Macete E, Milman J, et al. Efficacy of the RTS,S/AS02A vaccine against *Plasmodium falciparum* infection and disease in young African children: randomised controlled trial. Lancet 2004 Oct. 16-22; 364 (9443):1411-20). The follow-up periods in this trial and the 026 trial were not identical, slightly shorter in the infants than in the older children. Secondly, confidence intervals of the two estimates overlap.

TABLE 1

| Baseline characteristics | | |
|---|---|---|
| | Engerix-B ™ (n = 92) | RTS, S/AS02D (n = 93) |
| Age at first dose [weeks] | 8.3 (1.0) | 8.3 (1.4) |
| Gender | | |
| Female | 53 (58%) | 43 (46%) |
| Male | 39 (42%) | 50 (54%) |
| Area | | |
| Ilha Josina | 64 (70%) | 63 (68%) |
| Taninga | 28 (30%) | 30 (32%) |
| Distance [Kilometers] | | |
| 0-5 | 79 (86%) | 77 (83%) |
| 5-10 | 9 (10%) | 9 (10%) |
| 10-17 | 4 (4%) | 7 (7%) |

Data are mean (SD) or number of children (%)

TABLE 2

| Geometric mean titres (GMT) for Anti-CS and Anti-HBsAg | | | | |
|---|---|---|---|---|
| | Engerix-B ™ | | RTS, S/AS02D | |
| Geometric Mean Titre/Timing | n | value (95% CI) | n | value (95% CI) |
| Anti-circumsporozoite | | | | |
| Baseline | 77 | 0.4 (0.3; 0.4) | 76 | 0.4 (0.3; 0.5) |
| 30 days after third dose of RTS, S/AS02D or Engerix-B ™ | 68 | 0.3 (0.2; 0.3) | 71 | 199.9 (150.9; 264.7) |
| 106 days after third dose of RTS, S/AS02D or Engerix-B ™ | 61 | 0.4 (0.3; 0.5) | 53 | 58.8 (41.8; 82.8) |
| Anti-HBsAg | | | | |
| Baseline | 70 | 16.6 (11; 25) | 72 | 14 (9.6; 20.5) |
| 30 days after third dose of RTS, S/AS02D or Engerix-B ™ | 64 | 392.4 (297; 518.5) | 68 | 10081.6 (7394.9; 13744.4) |

TABLE 3

Vaccine efficacy from 14 days after third dose of Engerix-B ™ or RTS, S/AS02D until visit at month 6

| Outcome | Engerix-B ™ | | | RTS, S/AS02D | | | Vaccine efficacy | | p |
|---|---|---|---|---|---|---|---|---|---|
| | Events | PYAR | Rate | Events | PYAR | Rate | | (95% CI) | |
| Malaria infection | | | | | | | | | |
| First or only episode of parasitaemia >0 | 46 | 17.2 | 2.7 | 22 | 21.8 | 1.0 | 65.9% | (42.6%; 79.8%) | <0.001 |
| Clinical malaria | | | | | | | | | |
| First or only episode of fever and parasitaemia >500 per microliter | 22 | 19.6 | 1.1 | 9 | 22.6 | 0.4 | 65.8% | (25.3%; 84.4%) | 0.007 |
| First or only episode of fever or history of fever and parasitaemia >0 | 35 | 18.2 | 1.9 | 17 | 22.4 | 0.8 | 63.1% | (33.6%; 79.6%) | <0.001 |

PYAR = Person-years at risk. Vaccine efficacy estimates adjusted by distance from health facility and community.

TABLE 4

038 trial Efficacy ATP [over a year post dose 3 i.e. 3 to 14 months]

| | RTS, S/AS02D | | | | Engerix-B | | | | Point estimate of VE adjusted for covariates (%) |
|---|---|---|---|---|---|---|---|---|---|
| | Subjects (N) | No. of events | PYAR | Rate | Subjects (N) | No. of events | PYAR | Rate | |
| Disease 1 [a] | 93 | 36 | 61.83 | 0.582 | 92 | 45 | 51.27 | 0.878 | 33.122 |
| Disease 2 [b] | 93 | 45 | 57.26 | 0.786 | 92 | 57 | 41.34 | 1.379 | 41.978 |
| Disease 1 [c] | 93 | 58 | 72.69 | 0.80 | 92 | 74 | 68.83 | 1.08 | 26.2 |

| | Point estimate of VE adjusted for covariates | | | Point estimate of VE unadjusted for covariates | | | |
|---|---|---|---|---|---|---|---|
| | 95% CI | | P value | (%) | 95% CI | | P value |
| Disease 1 [a] | −4.056 | 57.017 | 0.074 | 34.313 | −1.838 | 57.631 | 0.060 |
| Disease 2 [b] | 13.754 | 60.965 | 0.007 | 41.893 | 14.044 | 60.719 | 0.007 |
| Disease 1 [c] | −16.6 | 53.3 | 0.1918 | 27.2 | −14.0 | 53.6 | 0.1645 |

PYAR: Episodes/Person Years at Risk; VE: Vaccine Efficacy (1-HR); CI: Confidence Interval; p value from Cox PH model; Poisson regression for multiple episodes
[a] first or only episodes; the presence of *P. falciparum* asexual parasitemia >500 per μL and the presence of fever ≥37.5° C.
[b] first or only episodes; any level of *P. falciparum* asexual parasitemia and the presence of fever ≥37.5° C. or a history of fever within 24 hours
[c] multiple episodes; the presence of *P. falciparum* asexual parasitemia >500 per μL and the presence of fever ≥37.5° C.
Adjusted estimates for area and distance from health center
ADI and PCD included

REFERENCES

1. Hay S I, Guerra C A, Tatem A J, Noor A M, Snow R W. The global distribution and population at risk of malaria: past, present, and future. The Lancet Infectious Diseases 2004; 4(6):327-336.
2. Breman J G, Alilio M S, Mills A. The intolerable burden of malaria: what's new, what's needed. Am J Trop Med Hyg 2004; 71(2_suppl):0-i-.
3. Klausner R, Alonso P. An attack on all fronts. Nature 2004; 430(7002):930-1.
4. Graves P, Gelband H. Vaccines for preventing malaria (pre-erythrocytic). *Cochrane Database of Systematic Reviews* 2006, Issue 4. Art. No.: CD006198 or Ballou W R, Arevalo-Herrera M, Carucci D, Richie T L, Corradin G, Diggs C, et al. Update on the clinical development of candidate malaria vaccines. Am J Trop Med Hyg 2004; 71(2_suppl):239-247.
5. Stoute J, Slaoui M, Heppner D, Momin P, Kester K, Desmons P, et al. A preliminary evaluation of a recombinant circumsporozoite protein vaccine against *Plasmodium falciparum* malaria. RTS,S Malaria Vaccine Evaluation Group. N Engl J Med 1997; 336(2):86-91.
6. Bojang K A, Milligan P J M, Pinder M, Vigneron L, Alloueche A, Kester K E, et al. Efficacy of RTS,S/AS02 malaria vaccine against *Plasmodium falciparum* infection in semi-immune adult men in The Gambia: a randomised trial. The Lancet 2001; 358(9297):1927-1934.
7. Bojang K A, Olodude F, Pinder M, Ofori-Anyinam O, Vigneron L, Fitzpatrick S, Njie F, Kassanga A, Leach A, Milman J, Rabinovich R, McAdam K P W J, Kester K E, Heppner D G, Cohen J D, Tomieporth N, and Milligan P J M. Safety and immunogenicity of RTS,S/AS02A candidate malaria vaccine in Gambian children. Vaccine published.
8. Macete E, Aponte J J, Guinovart C, Sacarlal J, Mandomando I, Espasa M, et al. Safety, reactogenicity and immunogenicty of the RTS,S/AS02A candidate malaria vaccine in children aged 1 to 4 years in Mozambique. Vaccine published.
9. Alonso P, Saúte F, Aponte J, Gómez-Olivé F, Nhacolo A, Thomson R, et al. Manhiça DSS, Mozambique. In: INDEPTH, ed. Population and Health in Developing Countries. Ottawa: International Development Research Centre, 2001: 189-195.
10. Dame J B, Williams J L, McCutchan T F, Weber J L, Wirtz R A, Hockmeyer W T, Maloy W L, Haynes J D, Schneider I, Roberts D, et al. Structure of the gene encoding the immunodominant surface antigen on the sporozoite of the human malaria parasite *Plasmodium falciparum*. Science. 1984; 225:593-9.

11. Young J F, Hockmeyer W T, Gross M, Ballou W R, Wirtz R A, Trosper J H, Beaudoin R L, Hollingdale M R, Miller L H, Diggs C L, et al. Expression of *Plasmodium falciparum* circumsporozoite proteins in *Escherichia coli* for potential use in a human malaria vaccine. Science 1985; 228:958-62.

12. Doherty J, Pinder M, Tornieporth N, Carton C, Vigneron L, Milligan P, et al. A phase I safety and immunogenicity trial with the candidate malaria vaccine RTS,S/SBAS2 in semi-immune adults in The Gambia. Am J Trop Med Hyg 1999; 61(6):865-868.

13. Loscertales M P, Roca A, Ventura P, Abascassamo F, Dos Santos F, Sitaube M, et al. Epidemiology and clinical presentation of respiratory syncytial virus infection in a rural area of southern Mozambique. Pediatr Infect Dis J 2002; 21:148-155.

14. Alonso P, Smith T, Schellenberg J, Masanja H, Mwankusye S, Urassa H, et al. Randomised trial of efficacy of SPf66 vaccine against *Plasmodium falciparum* malaria in children in southern Tanzania. The Lancet 1994; 344: 1175-81.

15. Saúte F, Aponte J, Almeda J, Ascaso C, Abellana R, Vaz N, et al. Malaria in southern Mozambique: malariometric indicators and malaria case definition in Manhiça district. in press.

16. World Health Organization. Management of severe malaria, a practical handbook. Second edition, 2000. http://mosquito.who.int/docs/hbsm.pdf 17. Therneau T M, Grambsch P M. Modeling Survival Data: Extending the Cox Model. New York: Springer, 2000.

18. Hess K R. Graphical methods for assessing violations of the proportional hazards assumption in Cox regression. Stat Med 1995; 14(15):1707-23.

19. Cytel Software Corporation. StatXact PROCs for SAS Users (version 6). Cambridge, Mass., USA.

20. SAS Institue Inc. SAS software (version 8). Cary, N.C., USA.

21. Stata Corporation. Stata Statistical Software (Release 8.0). College Station, Tex., USA 2003.

22. Sun P, Schwenk R, White K, Stoute J A, Cohen J, Ballou W R, Voss G, Kester K E, Heppner D G, Krzych U. Protective immunity induced with malaria vaccine, RTS,S, is linked to *Plasmodium falciparum* circumsporozoite protein-specific CD4(+) and CD8(+) T cells producing IFN-gamma J Immunol. 2003 Dec. 15; 171(12): 6961-7.

23. Stoute, J A, Kester K E, Krzych U, Wellde B T, Hall T, White K, Glenn G, Ockenhouse C F, Garçon N, Schwenk R, Lanar D E, Momin P, Golenda C, Slaoui M, Wortmann G, Cohen J, Ballou W R. Long Term Efficacy and Immune Responses Following Immunization with the RTS,S Malaria Vaccine. J Infect Dis 178:1139-44, 1998.

The invention claimed is:

1. A method for inducing an immune response against *Plasmodium falciparum* in an infant comprising
   a) selecting an infant from about 1 week old to about 50 weeks old and is at risk of malaria disease or infection; and
   b) administering an immunogenic composition comprising
      i) a fusion protein comprising a polypeptide comprising a *Plasmodium falciparum* circumsporozoite protein (CS) antigen or an immunogenic fragment thereof comprising substantially all the C-terminal portion of the CS protein and four or more tandem repeats of the CS protein immunodominant region; and
      hepatitis B surface antigen (HBsAg), and
      ii) a pharmaceutically acceptable adjuvant comprising 3-O-deacylated monophosphoryl lipid A (3D-MPL), and QS21,
   wherein the CS antigen is expressed at the pre-erythrocytic stage of malarial infection.

2. A method for treating, preventing or reducing the incidence of clinical malaria in an infant comprising
   a) selecting an infant from about 1 week old to about 50 weeks old and is at risk of malaria disease or infection; and
   b) administering an immunogenic composition comprising
      i) a fusion protein comprising a polypeptide comprising a *Plasmodium falciparum* circumsporozoite protein (CS) antigen or an immunogenic fragment thereof comprising substantially all the C-terminal portion of the CS protein and four or more tandem repeats of the CS protein immunodominant region; and
      hepatitis B surface antigen (HBsAg), and
      ii) a pharmaceutically acceptable adjuvant comprising 3-O-deacylated monophosphoryl lipid A (3D-MPL), and QS21,
   wherein the CS antigen is expressed at the pre-erythrocytic stage of malarial infection.

3. The method of claim 2, wherein the risk of developing clinical symptoms of malaria is reduced.

4. The method of claim 3, wherein the malaria is non-severe malaria.

5. The method of claim 2, wherein the immunogenic composition further comprises one or more additional antigens expressed on the sporozoite or pre-erthrocytic stage of malarial infection or an immunogenic fragment thereof.

6. The method of claim 2, wherein the additional antigen is selected from the group consisting of liver stage antigen-1 (LSA-1), liver stage antigen-3 (LSA-3), apical merozoite antigen-1 (AMA-1), merozoite surface protein-1 (MSP-1), thrombospondin related anonymous protein (TRAP) and Exp-1.

7. The method of claim 2, wherein the CS antigen comprises substantially all the C-terminal portion of the CS protein of *Plasmodium falciparum*, four or more tandem repeats of the CS protein immunodominant region, and the surface antigen from hepatitis B (HBsAg).

8. The method of claim 2, wherein the fusion protein is RTS.

9. The method of claim 8, wherein the immunogenic composition comprises RTS and S to form a composition of mixed particles RTS,S.

10. The method of claim 9, wherein the amount of RTS,S is 25 µg per dose.

11. The method of claim 2, wherein the adjuvant further comprises an oil in water emulsion.

12. The method of claim 2, wherein the adjuvant further comprises liposomes.

13. The method of claim 2, wherein the immunogenic composition is formulated as a pediatric dose.

14. The method of claim 13, wherein the pediatric dose is administered once, twice or three times.

15. The method of claim 14, wherein the pediatric dose is administered at two, three, four or five week intervals.

* * * * *